(12) United States Patent
Derrer et al.

(10) Patent No.: US 7,572,938 B2
(45) Date of Patent: Aug. 11, 2009

(54) PRECURSORS FOR KETONES AND ALDEHYDES

(75) Inventors: Samuel Derrer, Fällanden (CH); Markus Gautschi, Zeiningen (CH)

(73) Assignee: Givaudan SA, Vernier (CH)

( * ) Notice: Subject to any disclaimer, the term of this patent is extended or adjusted under 35 U.S.C. 154(b) by 1232 days.

(21) Appl. No.: 10/479,026

(22) PCT Filed: May 29, 2002

(86) PCT No.: PCT/CH02/00281
§ 371 (c)(1), (2), (4) Date: Nov. 26, 2003

(87) PCT Pub. No.: WO02/096850
PCT Pub. Date: Dec. 5, 2002

(65) Prior Publication Data
US 2004/0171516 A1   Sep. 2, 2004

(30) Foreign Application Priority Data
May 30, 2001   (EP)   .................................. 01112810

(51) Int. Cl.
C07C 45/00 (2006.01)
A61K 8/18 (2006.01)
(52) U.S. Cl. ...................... 568/309; 568/312; 512/24; 512/27
(58) Field of Classification Search ................. 568/309, 568/312; 512/24, 27
See application file for complete search history.

(56) References Cited

U.S. PATENT DOCUMENTS

| | | | |
|---|---|---|---|
| 3,409,674 A | 11/1968 | Moore | 260/592 |
| 3,715,293 A | 2/1973 | Sandner et al. | 204/159 |
| 4,251,341 A | 2/1981 | Felder et al. | 204/159.24 |
| 5,726,345 A | 3/1998 | Paget et al. | 560/238 |
| 6,133,228 A | 10/2000 | Pika et al. | 512/21 |
| 6,492,563 B2 * | 12/2002 | Gautschi et al. | 568/327 |
| 6,939,845 B2 * | 9/2005 | Gautschi et al. | 512/25 |

FOREIGN PATENT DOCUMENTS

| | | |
|---|---|---|
| DE | 0 222 217 A2 | 5/1987 |
| EP | 0887338 A1 | 12/1998 |
| EP | 0 983 990 A2 | 3/2000 |
| EP | 1 262 473 A1 | 12/2002 |

OTHER PUBLICATIONS

PCT International Search Report, dated Aug. 14, 2002, for PCT/CH02/00281.
XP-002182228 Database WPI Sec. Ch, Week 198306; Derwent Publications Ltd., London, GB; AN 1983-13363K -JP 57 210076 A (Ipposha Yushi Kogyo KK), Dec. 23, 1982 abstract.

* cited by examiner

*Primary Examiner*—Sikarl A Witherspoon
(74) *Attorney, Agent, or Firm*—Norris McLaughlin & Marcus, PA

(57) ABSTRACT

The present invention refers to compounds of formula I

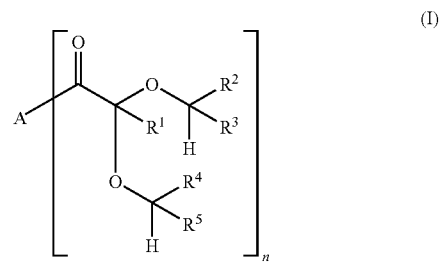

as precursors for a ketone of formula II,

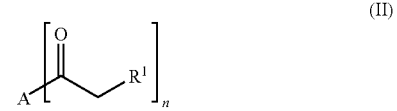

an aldehyde or ketone of formula III, and an aldehyde or ketone of formula IV,

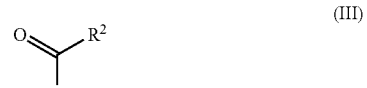

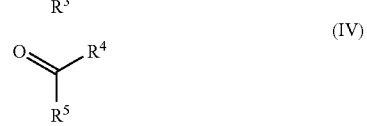

These compounds are useful in perfumery, especially in the fine and functional perfumery.

50 Claims, No Drawings

PRECURSORS FOR KETONES AND ALDEHYDES

The present invention relates to precursors for ketones and aldehydes which aldehydes and ketones are useful as fragrance materials in fragrance compositions.

A principal strategy currently employed in imparting odors to consumer products is the admixing of the fragrance directly into the product. There are, however, several drawbacks to this strategy. The fragrance material can be too volatile and/or too soluble, resulting in fragrance loss during manufacturing, storage, and use. Many fragrance materials are also unstable over time. This again results in loss during storage.

In many consumer products it is desirable for the fragrance to be released slowly over time. Micro-encapsulation and inclusion complexes with cyclodextrins have been used to help decrease volatility, improve stability and provide slow-release properties. However, these methods are for a number of reasons often not successful. In addition, cyclodextrins can be too expensive for use in many applications.

It is therefore desirable to have a fragrance delivery system which is capable of releasing the fragrant compound or compounds in a controlled manner, maintaining a desired smell over a prolonged period of time.

Precursors for the delivery of organoleptic compounds, especially for flavours, fragrances and masking agents, are described in EP-A 0 936 211. This delivery system releases one or more odoriferous compounds upon exposure to light and/or UV irradiation. Using this system in various consumer products leads to a prolonged perception of the fragrant compound(s) to be released. WO 99/60990 describes fragrance precursors which release fragrant alcohols, aldehydes or ketones upon exposure to light.

The majority of fragrant compounds with odors accepted by the public are aldehydes and ketones. In fragrance compositions these aldehydes and ketones play an important role in imparting, for example, fresh, green, floral, aldehydic and hesperidic aspects to the composition. In particular, aldehydes are fast degraded in alkaline and oxidative environments thereby losing their fragrant characteristic and, consequently, the desired fresh, green, floral, aldehydic and hesperidic aspects of the perfume. Therefore, they are of limited use for laundry care products, especially detergents.

Accordingly there is a need to provide compounds which are stable in alkaline and oxidative environments, especially in laundry care products, and which may deposit onto treated surfaces with high substantivity thereby to release compounds, e.g. aldehydes and ketones useful as fragrance materials in fragrance compositions, upon exposure to an exogenous stimulus.

Therefor in a first aspect the present invention relates to the use of a compound of the formula I

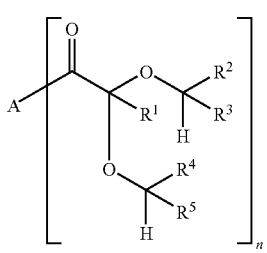

(I)

as a precursor for a ketone of the formula II,

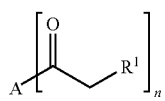

(II)

an aldehyde or ketone of the formula III comprising up to 20 carbon atoms,

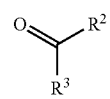

(III)

and an aldehyde or ketone of the formula IV comprising up to 20 carbon atoms,

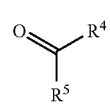

(IV)

wherein

A is an aromatic, e.g. phenyl, or a heteroaromatic ring, for example a 5 or 6 membered heteroaromatic ring, e.g. pyridyl, pyryl, imidazilyl; or an aromatic or heteroaromatic ring as aforementioned substituted with one or more residues selected from the group of alkyl, aryl, aralkyl, alkenyl, alkynyl, —OH, —O-alkyl, -alkoxyalkoxy, —O-aralkyl, —O-aryl, —O-acyl, —NO$_2$, —NH$_2$, —NH-alkyl, —N(alkyl)$_2$, —NH-acyl, —N(acyl)$_2$, —CN, —SH, —S-alkyl, —S-aryl and a halogen atom, selected from fluorine, chlorine or bromine; or an aromatic or heteroaromatic ring as aformentioned bearing a residue that together with the carbon atoms to which it is attached forms an aromatic or alicyclic ring, for example 5 and 6 membered rings, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues, $R^1$ represents hydrogen, alkyl, alkenyl, alkynyl, acyl, or aryl residue, and said residues may comprise one or more oxygen atom(s), $R^2$, $R^3$, $R^4$, $R^5$ represent independently hydrogen, alkyl, alkenyl, alkynyl, cycloalkyl, cycloalkenyl or aromatic residues, and said residues may comprise one or more oxygen atoms, or $R^2$ and $R^3$ together with the carbon atom to which they are attached may form a 4 to 18 membered carbocyclic ring, optionally substituted by an alkyl, alkenyl or alkynyl residue having up to 10 carbon atoms, and the ring and residues may comprise one or more oxygen atoms, $R^4$ and $R^5$ together with the carbon atom to which they are attached may form a 4 to 18 membered carbocyclic ring, optionally substituted by an alkyl, alkenyl or alkynyl residue having up to 10 carbon atoms, and the ring and residues may comprise one or more oxygen atoms, and n is an integer from 1 to 3.

As used in relation to compounds of formula I unless otherwise indicated "alkyl" refers to $C_1$-$C_{20}$, preferably $C_1$-$C_4$, e.g. methyl, ethyl, isobutyl, or $C_5$-$C_{18}$, e.g. hexyl, (2-ethylhexyl)-; "aryl" refers to $C_6$-$C_{20}$, preferably $C_6$-$C_{10}$, e.g. phenyl, naphthyl, or $C_{11}$-$C_{15}$, e.g. anthryl; "aralkyl" refers to $C_7$-$C_{20}$, preferably $C_7$-$C_{15}$, e.g. benzyl, phenylethyl, phenylpropyl; "alkenyl" refers to $C_2$-$C_{20}$, e.g. vinyl, vinylpropenyl, isobutenyl, preferably $C_5$-$C_{17}$, e.g. 9-decenyl, 10-undecenyl, 3,7-dimethyl-6-octenyl; "alkynyl" refers to $C_2$-$C_{20}$, preferably $C_2$-$C_{10}$, e.g. ethynyl, propynyl, heptynyl, octynyl, 6-methyl-heptynyl; "acyl" refers to $C_1$-$C_{20}$, preferably $C_2$-$C_{10}$, e.g. acetyl, benzoyl, or $C_{11}$-$C_{18}$, e.g. dodecanoyl, hexadecanoyl; "cycloalkyl" refers to $C_3$-$C_{20}$, preferably $C_4$-$C_8$, e.g. cyclobutyl, cycloheptyl, 3,3-dimethylcyclohexyl, or $C_9$-$C_{18}$, e.g. cyclodecanyl; "cycloalkenyl" refers to $C_3$-$C_{20}$, preferably $C_4$-$C_8$, e.g. cyclopentadienyl, cyclooctatetraenyl, 2,2,3-trimethyl-3-cyclopentenyl, cyclooctenyl or $C_9$-$C_{18}$, e.g. cyclododecenyl, 2,4,5-trimethyl-3-cyclohexenyl, cyclopentadecenyl; and "alkoxyalkoxy" refers to $C_3$-$C_{20}$, preferably $C_3$-$C_{10}$, e.g. methoxyethoxy, methoxy-(ethoxy)$_2$, methoxypropoxy or $C_{11}$-$C_{18}$, e.g. methoxy-(ethoxy)$_5$.

The compounds of formula I release upon exposure to light volatile aldehydes and ketones of formula III and IV and ketones of formula II. Since the compounds of formula I are stable in alkaline and oxidative environment and show high substantivity, they are excellently adapted for use in detergent and laundry care products.

The compounds of formula I are slowly cleaved when exposed to light, in particular daylight. Upon absorption of energy from said light, the compounds of formula I undergo twice a Norrish Type II photoreaction which leads to the release of a ketone of formula II and an aldehyde and/or ketone of formula III and IV.

The compounds of formula I cleaved particularly well in light having a wavelength range of 200 nm to 800 nm, although irradiation with light having a wavelength from about 250 nm to 400 nm is preferred.

The release of the above mentioned compounds occurs for example upon exposure to sunlight penetrating through ordinary windows and being not particularly rich in UV irradiation. It is needless to say that upon exposure to bright sunlight, in particular outdoors, the release of the compounds of formula II, III and IV will occur faster and to a greater extent than upon exposure to room light of natural or artificial origin inside a building. The cleavage of the compounds of formula I can also be initiated by an appropriate lamp, for example a sun-tanning lamp.

The photoreaction of the compounds of formula I involves, in a first step, the absorption of light by the keto-group followed by abstraction of the acetal-H atom and subsequent cleavage of the resulting 1,4-di-radical (Scheme A). It has been found that the residue A of the compounds of formula I plays an important role in this photoreaction as it influences the absorption maximum $\lambda_{max}$ of the keto-group. Therefore, the cleavage properties of the compounds of formula I can be modified by variation of A.

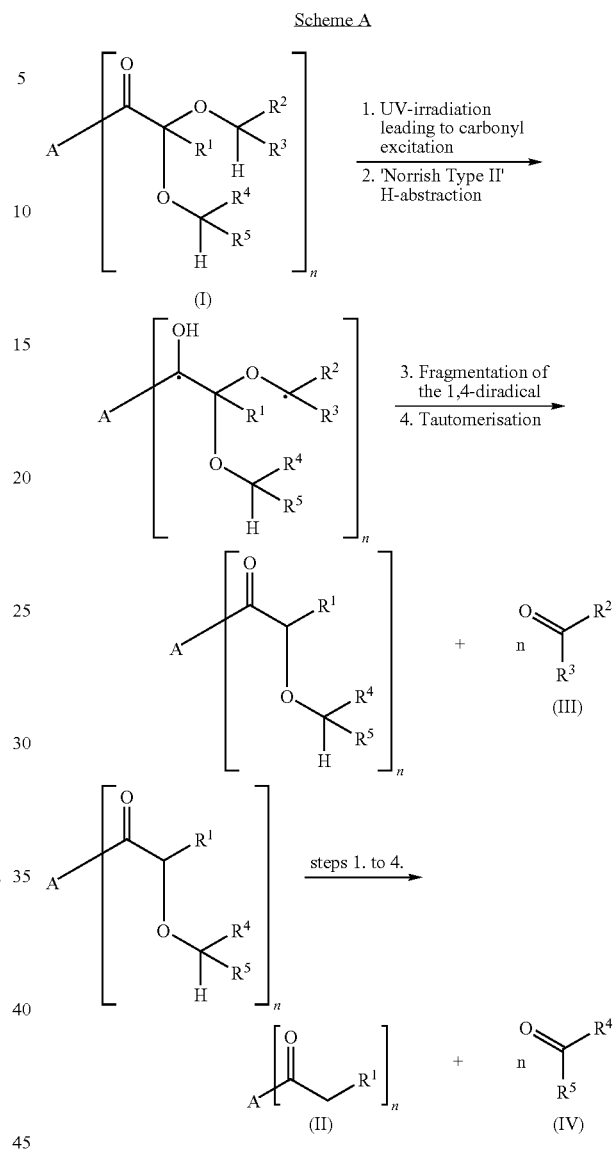

Scheme A

The ketone of formula II can be a ketone with fragrant properties and/or can have the function to stabilize the chemical structure, and/or can be a substantivity and/or light-absorbance-enhancing element of a compound of formula I.

A ketone of formula II having fragrant properties is a compound known to a person skilled in the art as being a useful ingredient for the formulation of perfumes or perfumed articles. Non-limiting examples of said ketones are:
1-(4-methoxyphenyl)-ethanone (acetanisole)*,
1-phenyl-ethanone (acetophenone),
1-(6-tert-butyl-1,1-dimethyl-indan-4-yl)-ethanone*,
1-(2,4-dimethylphenyl)-ethanone (dimethyl acetophenone)*,
1-(3,5,5,6,8,8-hexamethyl-5,6,7,8-tetrahydro-naphthalen-2-yl)-ethanone**,
1-(5,6,7,8-tetrahydro-2-naphthalenyl)-ethanone*,
3-methyl-1-(4-methylphenyl)-4-hexen-1-one,
1-phenyl-4-penten-1-one,
1-(1,1,2,3,3-pentamethyl-indan-5-yl)-ethanone*,
1-(2-naphthalenyl)-ethanone*,
1-(1,1,2,3,3,6-hexamethyl-indan-5-yl)-ethanone*, 1-phenyl-propan-2-one (propiophenone),
1-[1,1,2,6-tetra-methyl-3-(1-methylethyl)-indan-5-yl]-ethanone**,
1-(3,5,5,8,8-pentamethyl-5,6,7,8-tetrahydro-naphthalen-2-yl)-ethanone*,
1-(3-ethyl-5,5,8,8-tetramethyl-5,6,7,8-tetrahydro-naphthalen-2-yl)-ethanone*, whereby * indicates the preferred ketones and ** indicate the more preferred ketones.

It is obvious to the person skilled in the art that the above list is illustrative and that the present invention relates to many other ketones of formula II, more particular ketones having fragrant properties.

Aldehydes of formula III and IV represent an important class of perfumery raw materials and comprise compounds of a vast structural variety. Aldehydes of formula III and IV contribute to the odor and aroma of various flowers and fruits and are known to be useful ingredients for the formulation of perfumes or perfumed articles. In the following list non-limiting examples of such aldehydes are given:
2,6,10-trimethylundec-9-enal*,
8,8-dimethyl-1,2,3,4,5,6,7,8-octahydro-naphthalene-2-carbaldehyde,
(4-isopropyl-phenyl)-ethanal,
2,4-dimethyl-cyclohex-3-ene-1-carbaldehyde*,
1,3,5-trimethyl-cyclohex-1-ene-4-carbaldehyde*,
4-(4-hydroxy-4-methylpentyl)-cyclohex-3-ene-1-carbaldehyde*,
hex-2-enal*,
3,5,5-trimethyl-hexanal,
heptanal*,
2,6-dimethyl-hept-5-enal*,
decanal**,
dec-9-enal,
dec-4-en-1-al,
2-methyl-decanal*,
undec-10-en-1-al**,
undecanal*,
dodecanal**,
2-methyl-undecanal**,
tridecanal,
tridec-2-enal,
octanal**,
nonanal*,
non-2-enal,
undec-9-enal**,
2-phenyl-propanal*,
2-(4-methyl-phenyl)-ethanal*,
3,7-dimethyl-octanal*,
dihydrofarnesal**,
7-hydroxy-3,7-dimethyl-octanal*,
2,6-dimethyl-oct-5-en-1-al,
3-(3-isopropyl-phenyl)-butanal**,
2-(3,7-dimethyl-oct-6-en-oxy)-ethanal,
4-(4-methyl-pent-3-enyl)-cyclohex-3-ene-1-carbaldehyde*,
2,3,5,5,-tetramethyl-hexanal,
longifolic aldehyde,
2-methyl-4-(2,6,6-trimethylcyclohex-2-en-1-yl)-butanal*,
2-methyl-3-(4-tert-butylphenyl)-propanal**,
3-(4-tert-butyl-phenyl)-propanal*,
2-(4-isopropyl-phenyl)-propanal,
3-(benzo[1,3]dioxol-5-yl)-2-methyl-propanal*,
3,7-dimethyl-oct-6-ene-1-al*,
2-methyl-3-(4-isopropylphenyl)-propanal*,
4-tert-butyl-cyclohexane-1-carbaldehyde,
4-(octahydro-4,7-methano-5H-inden-5-ylidene)-butanal,
(3,7-dimethyl-oct-6-enyloxy)-ethanal**,
(2E,6Z)-nonadienal*,
2,4-dimethyl-2,6-heptadienal,
(E)-dec-2-enal*,
dodec-2-enal*,
3,7-dimethyl-octa-2,6-dienal*,
2,4-diethyl-hepta-2,6-dienal,
3,7-dimethyl-nona-2,6-dienal*,
3-propyl-hept-2-enal,
4-isopropenyl-cyclohex-1-ene-1-carbaldehyde, whereby * indicates the preferred aldehydes and ** indicate the more preferred aldehydes.

Ketones of formula III and IV represent another important class of perfumery raw materials and comprise compounds of a vast structural variety. Ketones of formula III and IV contribute to the odor and aroma of various flowers and fruits and are known to be useful ingredients for the formulation of perfumes or perfumed articles. In the following list non-limiting examples of such ketones are given:
2,5-dimethyl-oct-2-en-6-one**,
4-(2,6,6-trimethylcyclohex-1-en-1-yl)-butan-2-one*,
4-(2,6,6-trimethylcyclohex-2-en-1-yl)-butan-2-one*,
4-(2,5,6,6-tetramethyl-2-cyclohexen-1-yl)-but-3-en-2-one*,
4-(2,6,6-trimethyl-2-cyclohexen-1-yl)-3-methyl-but-3-en-2-one*,
5-isopropenyl-2-methyl-cyclohex-2-enone*,
1-(4-hydroxyphenyl)-butan-3-one**,
4-(1,3-benzodioxole-5-yl)-butan-2-one**,
2-heptyl-cyclopentanone**,
nonan-2-one**,
octan-2-one**,
heptan-2-one**,
undecan-2-one**,
4-phenyl-butan-2-one**,
6-methyl-hept-5-en-2-one**,
2-(sec-butyl)-cyclohexanone**,
2-hexyl-cyclopent-2-en-1-one**,
2-(isopropyl)-5-methyl-cyclohexanone*,
5-methyl-2-propyl-cyclohexanone**,
4-(1,1-dimethylpropyl)-cyclohexanone**,
6,10-dimethyl-undeca-5,9-dien-2-one**,
(3-oxo-2-pentyl-cyclopentyl)-acetic acid methyl ester**,
3-(2-Oxo-propyl)-2-pentyl-cyclopentanone**,
cis-1-(1,2,3,4,5,6,7,8-octahydro-1,2,8,8-tetramethyl-2-naphthalenyl)-ethanone*,
1-(2,3,8,8-tetramethyl-1,2,3,4,5,6,7,8-octahydro-naphthalen-2-yl)-ethanone*,
1-cyclohex-2-enyl-2,4-dimethyl-pent-2-en-1-one*,
2-hexyl-cyclopent-2-en-1-one*,
2-pentyl-cyclopent-2-enone,
3-methyl-2-pentyl-cyclopent-2-enone*,
2-hexylidene-cyclopentanone*,
3,5-diethyl-5,6-dimethyl-cyclohex-2-enone*,
6-isopropenyl-4,4a-dimethyl-4,4a,5,6,7,8-hexahydro-3H-naphthalen-2-one*,
3-methyl-6-propylidenecyclohexanone*,
4-(1-methylethyl)-cyclohex-2-en-1-one,
(E)-oct-3-en-2-one,
1-(3,6,8,8-tetramethyl-2,3,4,7,8,8a-hexahydro-1H-3a,7-methano-azulen-5-yl)-ethanone*,
1-(3,3-dimethyl-cyclohex-1-enyl)-ethanone*,
1-(2,4,6-trimethylcyclohex-3-en-1-yl)-but-1-en-3-one,
2-(3-methylbut-2-en-1-yl)-3-methyl-cyclopent-2-en-1-one,
3-methyl-5-(2,2,3-trimethyl-cyclopent-3-en-1-yl)-pent-3-en-2-one*,
5-butylidene-2,2,4-trimethylcyclopentanone, 1,1,2,3,3-pentamethyl-1,2,3,5,6,7-hexahydro-inden-4-one*,
3-methyl-5-propyl-cyclohex-2-en-1-one*,
6-isopropyl-4,4a,5,6,7,8-hexahydro-3H-naphthalen-2-one,
3,5,5-trimethyl-cyclohex-2-en-1,4-dione*,
(E)-5-methyl-3-hepten-4-one,
acetyl diisoamylene*,
dec-3-en-2-one,
4-(2-ethyl-3,6,6-trimethyl-cyclohex-2-enyl)-but-2-enal,
1-(5,5-dimethyl-1(6)-cyclohexen-1-yl)-4-penten-1-one*,
1-(2,6,6-trimethyl-1-cyclohexen-1-yl)-but-2-en-1-one*,
1-(2,6,6-trimethyl-2-cyclohexen-1-yl)-but-2-en-1-one*,
1-(2,6,6-trimethyl-3-cyclohexen-1-yl)-but-2-en-1-one*,
4-(2,5,6,6-tetramethyl-2-cyclohexen-1-yl)-but-3-en-2-one*,
2,4,4,5,5-pentamethyl-1-cyclopentene-1-yl-ethanone*,
cyclohexadec-5-enone**,
cyclopentadecanone**,
3-methyl-cyclopentadecanone**,
7-methyl-3,4-dihydro-2H-1,5-benzodioxepin-3-one**, whereby * indicates the preferred ketones and ** indicate the more preferred ketones.

Additional aldehydes and ketones of formula II, III and IV having fragrant properties are e.g. described in "Perfume and Flavor Chemicals", S. Arctander Ed., Vol. I & II, Allured Publishing Corporation, Carol Stream, USA, 1994; and in "Common Fragrance and Flavor Materials", K. Bauer, D. Garbe and H. Surburg, Eds., Wiley-VCH, 3$^{rd}$ Edition, Weinheim, 1997.

Many of the aldehydes and ketones of formula III and IV described above, which are of pleasant odor, are rather volatile, and/or unstable in aggressive media, and/or considerably water soluble.

The compounds of formula I are not, or only slightly, volatile. The ketones of formula II and the aldehydes and ketones of formula III and IV are released only upon exposure to light, and especially daylight. The photochemical cleavage provides, over days and weeks, perceptible amounts of aldehydes and ketones. The period depends inter alia on the amount or concentration of the compounds of formula I applied, the duration of exposure to light, its intensity and its wavelength.

Aldehydes and ketones of formula III and IV are prone to degradation, especially in alkaline and bleaching (oxidising) products such as detergents. They are also considerably water soluble and to some extent are washed away in washing/ cleaning processes. These facts may result in considerable loss of perfume and in particular the notes imparted paricularly by aldehydes.

Today's consumers select a certain product not only based on functional performance but also based on the odor. From the foregoing it is evident that systems for introducing a variety of fragrance accords to products having alkaline pH and bleaching acivity are desirable. The compounds of formula I have the advantage that they are not, or only slightly, volatile and chemically stable in consumer products having alkaline and/or neutral pH and/or bleaching activity. A compound of formula I added to a powder detergent, is stable in the detergent powder throughout storage. During the washing cycle (alkaline pH) and the rinsing cycle (neutral pH) the compound is deposited on the fabric surface. It is only upon exposure of the fabric to light, for example during line-drying in the sun, that the release of the ketone of formula II and the aldehydes and ketones of formula III and IV is started.

It has been mentioned above that aldehydes and ketones of formula III and IV are rather volatile compounds. This is especially true for low molecular weight aldehydes and ketones being substituted by aliphatic chains, for example aldehydes and ketones having a molecular weight less than 200. Furthermore, they are to a certain extent water soluble and are, therefore, lost to some extent during the washing/ rinsing cycle if introduced directly. The compounds of formula I have the advantage that they have good substantivity on different substrates, especially on fabrics. Furthermore, the compounds of formula I are not, or only slightly, volatile thus no loss occurs during storage. By means of the compounds of formula I highly volatile aldehydes and ketones of formula III and IV with low substantivity may be successfully applied to achieve a long lasting pleasant odor. The volatile aldehydes and ketones are produced in situ after application of the compound of formula I onto a fabric during the washing cycle upon activation by light.

In the compounds of formula I the moiety derived from a ketone of formula II brings three advantages: it introduces stability as well as substantivity to the compounds and upon activation by light it can exhibit fragrant properties.

The compounds of formula I are advantageously prepared via the following methods. Firstly, when R$^1$ is H, the ketone of formula II is oxidised with concentrated aqueous hydrobromic acid in dimethyl sulfoxide (H. Brawner Floyd et al., J. Org. Chem., 1985, 50, 5022-5027) to give the hydrated arylglyoxal. This is converted into the corresponding diethyl acetal under mildly acid conditions. Alternatively, the corresponding dimethyl acetal can be accessed directly by the treatment of the ketone of formula II with diphenyldiselenide and ammonium peroxydisulfate in methanol (M. Tiecco et al., J. Org. Chem., 1990, 55, 4523-4528). Trans-acetalisation with the alcohol derived from aldehydes or ketones of formula III and IV under mildly acidic conditions yields the compound of formula I. These syntheses are illustrated in scheme I:

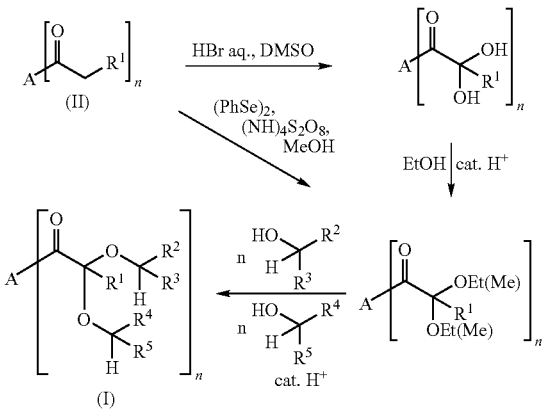

According to a further method the ketone of formula II is halogenated with for example sulfuryl halide in dimethylformamide. If A in formula II contain nitrogen substituents such as amines, the bromination in concentrated sulfuric acid can be employed (Z. Diwu et al., Tetrahedron Lett., 1998, 39, 4987-4990). The intermediate dihalide can be substituted with sodium methylate or potassium carbonate in methanol. Mildly acidic trans-acetalisation with the alcohol derived from aldehydes and ketones of the formula III and IV then affords the compounds of formula I. The syntheses via this route is illustrated in scheme II:

Scheme II

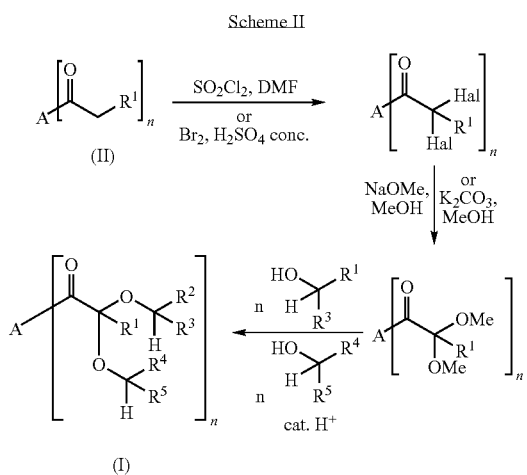

Preferred compounds of the formula I are compounds releasing aldehydes of the formula III and IV, wherein n=1, $R^2$ and $R^4$ are independently an alkyl, alkenyl, alkynyl residue having 5 to 17 carbon atoms, and $R^3$ and $R^5$ are H. Most preferred compounds are those releasing fatty aldehydes having 6 to 13 carbon atoms and 2-methyl-undecanal.

Other preferred compounds of formula I include compounds wherein n=1, $R^2$ and $R^4$ are independently the residue of a cyclic or acyclic terpene or of a terpenoic aldehyde, i.e. a terpene derived aldehyde, e.g. an aldehyde obtained in one or more synthetic steps from terpenoids, having 4 to 15 carbon atoms, and $R^3$ and $R^5$ are H. Most preferred compounds are those releasing citronellal, citral, 7-hydroxydihydrocitronellal, 7-methoxydihydro-citronellal and 2,6,10-trimethyl-9-undecenal [ADOXAL[1)]].

Other preferred compounds of formula I include compounds wherein n=1, $R^2$ and $R^4$ are cycloaliphatic residues having 4 to 15 carbon atoms, and $R^3$ and $R^5$ are H. Most preferred compounds are those releasing 2,4-dimethyl-3-cyclohexene carboxaldehyde [CYCLAL C[1)]], 4-(4-methyl-3-penten-1-yl)-3-cyclohexene carboxaldehyde [MYRALDEN[1)]], and 4-(4-hydroxy-4-methylpentyl)-3-cyclohexene carboxaldehyde [LYRAL[3)]].

Other preferred compounds are those wherein n=1, $R^2$ and $R^4$ are independently a substituted or unsubstituted aromatic residue having 4 to 15 carbon atoms, and $R^3$ and $R^5$ are H. Most preferred compounds are those releasing benzaldehyde, 4-methoxybenzaldehyde (p-anisaldehyde), 3,4-methylenedioxybenzaldehyde (heliotropine, piperonal), phenylacetaldehyde, 3-phenylpropanal, 2-phenylpropanal, 4-methylphenylacetaldehyde, 3-(4-ethylphenyl)-2,2-dimethylpropanal [FLORALOZONE[3)]], 2-methyl-3-(4-isopropylphenyl)-propanal (Cyclamenaldehyde), 2-methyl-3-(4-tert-butylphenyl)-propanal [LILIAL[1)]], cinnamaldehyde, 2-pentyl-3-phenyl-2-propenal (α-amyl-cinnamaldehyde), 2-hexyl-3-phenyl-2-propenal (α-hexyl-cinnamaldehyde), 4-hydroxy-3-methoxybenzaldehyde (vanillin) and 3-ethoxy-4-hydroxybenzaldehyde (ethylvanillin).

Other preferred compounds are those wherein n=1, $R^2$ and $R^3$ are alkyl, alkenyl or alkynyl residues having together 5 to 17 carbon atoms, and $R^4$ and $R^5$ are alkyl, alkenyl or alkynyl residues having together 5 to 17 carbon atoms. A most preferred compound is one that releases 3-octanone.

Other preferred compounds of formula I include compounds wherein n=1 and $R^2$, $R^3$, $R^4$ and $R^5$ are the residues of cyclic or acyclic terpene or terpenoic ketones, i.e. terpene derived ketones, e.g. a ketone obtained in one or more synthetic steps from terpenoids, having 4 to 15 carbon atoms. Most preferred compounds are those releasing 6,10-dimethyl-5,9-undecadien-2-one (geranylacetone), (menthones and isomenthones), 1,8-p-menthadien-6-one (carvone), 1,7,7-trimethylbicyclo[2.2.1]heptan-2-one (camphor), 1,3,3-trimethylbicyclo[2.2.1]heptan-2-one (fenchone), 4-(2,6,6-trimethylcyclohexenyl)-3-butene-2-ones and 4-(2,6,6-trimethylcyclohexenyl)-butan-2-ones (ionones and dihydroionones), 1-(2,6,6-trimethylcyclohexenyl)-2-butene-1-ones (damascones), 5,6-dimethyl-8-isopropenylbicyclo[4.4.0]-dec-1-en-3-one (nootkatone) and cedryl methyl ketone.

Other preferred compounds are those wherein n=1, and $R^2$, $R^3$, $R^4$, and $R^5$ are the residues of cycloaliphatic ketones having 8 to 18 carbon atoms. Most preferred compounds are those releasing 2-pentylcyclopentanone [DELPHONE[2)]], 2-heptylcyclopentanone [ALISMONE (Haarmann & Reimer GmbH, Germany)], 2,2,5-trimethyl-5-pentylcyclopentanone [VELUTONE[2)]], 3-methyl-2-pentyl-2-cyclopenten-1-one (dihydrojasmone), 3-methyl-2-(2-cis-penten-1-yl)-2-cyclopenten-1-one (cis-jasmone), 4-tert-pentylcyclohexanone [ORIVONE[3)]], 6,7-dihydro-1,1,2,3,3-pentamethyl-4(5H)-indanone [CASHMERAN[3)]], cyclopentadecanone [EXALTONE[2)]], 3-methylcyclopentadecanone [MUSCENONE[2)]], 5-cyclohexadecen-1-one, 9-cycloheptadecen-1-one [CIVETTONE[2)]], 5-cyclohexadecen-1-one [VELVIONE], 1-(5,5-dimethyl-1-cyclohexen-1-yl)-4-penten-1-one [DYNACONE[2)]] and 1-(1,2,3,4,5,6,7,8-octahydro-2,3,8,8-tetramethyl-2-naphthalenyl)-ethanone [ISO E SUPER[3)]]

whereby [1)] indicates Givaudan SA, Vernier, Switzerland, [2)] indicates Firmenich SA, Switzerland, and [3)] indicates International Flavors & Fragrances, USA as supplier.

Other preferred compounds are those wherein n=1, $R^2$, $R^3$, $R^4$, and $R^5$ are the residues of araliphatic ketones having 8 to 18 carbon atoms. Most preferred compounds are those releasing 4-(4-hydroxyphenyl)-2-butanone (raspberry ketone) and 4-phenyl-2-butanone (benzylacetone).

Other preferred compounds of formula I include compounds wherein n=1 and $R^1$=H. Most preferred are compounds which upon cleavage of these compounds release a ketone of formula II wherein said ketone is an aryl methyl ketone.

Other preferred compounds are those wherein n=1 and $R^1$ represents an alkyl, alkenyl, aralkyl or aryl residue having 1 to 20 carbon atoms. Most preferred are compounds which upon cleavage of these compounds release propiophenone.

Other preferred compounds of formula I are compounds wherein n=1, $R^1$=H, and A is an aromatic ring, e.g. phenyl; or an aromatic ring substituted with one or more residues selected from the group of alkyl, alkenyl, alkynyl, and alkoxy; or an aromatic ring, e.g. phenyl, bearing a residue that together with the carbon atoms to which it is attached forms an aromatic or alicyclic ring, for example 5 and 6 membered rings, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues. Most preferred compounds are those releasing a ketone of formula II selected from 1-phenyl-ethanone (acetophenone), 1-(4-methoxyphenyl)-ethanone (acetanisole), 2,4-dimethylphenyl-ethanone, 1-(4-methoxyphenyl)-ethanone, 1-(2-naphtalenyl)-ethanone, 4-acetyl-6-tert-butyl-1,1-dimethyl-indan, 1-(5,6,7,8-tetrahydro-3',5',5', 6',8',8'-hexamethyl-2-naphthalenyl)-ethanone, 1-(5,6,7,8- tetrahydro-3',5',5',8',8'-pentamethyl-2-naphthalenyl)-ethanone, 1-(5,6,7,8-tetrahydro-3'-ethyl-5',5',8',8'-tetramethyl-2-naphthalenyl)-ethanone, 1-(2,3-dihydro-1',1',2',3',3',6'-hexamethyl-1H-inden-5-yl)-ethanone, 1-[2,3-dihydro-1',1',2',6'-tetramethyl-3-(1-methylethyl)-1H-inden-5-yl]-ethanone, 5-acetyl-1,1,2,3,3-pentamethyl-indane, and 1-(5,6,7,8-tetrahydro-2-naphthalenyl)-ethanone.

Other preferred compounds are those wherein n=1, $R^1$=H and A is a heteroaromatic ring, for example a 5 or 6 membered heteroaromatic ring, e.g. pyridyl, pyryl, imidazilyl; or an aromatic, e.g. phenyl or heteroaromatic ring, e.g. pyridyl, pyryl, imidazilyl, substituted with one or more residues selected from the group —OH, —O-alkyl, -alkoxyalkoxy, —O-aralkyl, —O-aryl, —O-acyl, —$NO_2$, —$NH_2$, —NH-alkyl, —N(alkyl)$_2$, —NH-acyl, —N(acyl)$_2$, —SH, —S-alkyl, —S-aryl; or an aromatic or heteroaromatic ring as aforementioned bearing a residue that together with the carbon atoms to which it is attached forms an aromatic or alicyclic ring, for example 5 and 6 membered rings, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues. Most preferred compounds are those releasing a ketone of formula II selected from 4-alkoxy-acetophenones, 4-alkylthioacetophenones, 4-dialkylamino-acetophenones, 4-acylamino-acetophenones, 4-diacylamino-acetophenones, 31,41-(methylenedioxy)-acetophenone, 2,4-dialkoxy-acetophenones, 4-(2-methoxyethoxy)-acetophenone, 2,4-di-(2-methoxyethoxy)-acetophenone, 4-[2-(2-methoxyethoxy)-ethoxy]-acetophenone, 2,4-di-[2-(2-methoxyethoxy)-ethoxy]-acetophenone, 1-(2,3-dihydro-benzo[1,4]dioxin-6-yl)-ethanone.

Other preferred compounds of formula I are those, wherein the released compounds of formula III and IV are the same.

Those compounds of the formula I are especially preferred, wherein n is 1, $R^1$ is H, methyl, phenyl, A is phenyl, 6-tert-butyl-1,1-dimethyl-indan-4-yl, 2,4-dimethylphenyl, 3,5,5,6,8,8-hexamethyl-5,6,7,8-tetrahydro-naphthalen-2-yl, 5,6,7,8-tetrahydro-2-naphthalenyl, 1,1,2,3,3-pentamethyl-indan-5-yl, 2-naphthalenyl, 1,1,2,3,3,6-hexamethyl-indan-5-yl, 1,1,2,6-tetra-methyl-3-(1-methylethyl)-indan-5-yl, 3,5,5,8,8-pentamethyl-5,6,7,8-tetrahydro-naphthalen-2-yl, 3-ethyl-5,5,8,8-tetramethyl-5,6,7,8-tetrahydro-naphthalen-2-yl, 4-alkoxy-phenyl, 4-dialkylamino-phenyl, 4-acylamino-phenyl, 4-diacylamino-phenyl, 3,4-(methylenedioxy)-phenyl, 3,4-dialkoxy-phenyl, 4-(2-methoxyethoxy)-phenyl, 3,4-di-(2-methoxyethoxy)-phenyl, 4-[2-(2-methoxyethoxy)-ethoxy]-phenyl, 3,4-di-[2-(2-methoxyethoxy)-ethoxy]-phenyl, 2,3-dihydro-benzo[1,4]dioxin-6-yl, and $R^2$=$R^4$ are H, and $R^3$=$R^5$ are 6,10-dimethylundec-9-ene-2-yl, 2,4-dimethyl-cyclohex-3-ene-1-yl, 1,3,5-trimethyl-cyclohex-1-ene-4-yl, 4-(4-hydroxy-4-methyl-pentyl)-cyclohex-3-ene-1-yl, pent-1-enyl, hexyl, 6-methyl-hept-5-ene-2-yl, nonyl, 2-decyl, 9-decenyl, decyl, undecyl, 2-undecyl, heptyl, octyl, 8-decenyl, 1-phenyl-ethyl, (4-methyl-phenyl)-methyl, 2,6-dimethyl-heptyl, 2,6,10-trimethyl-undeca-5,9-dienyl, 2,6-dimethyl-6-hydroxy-heptyl, 2-(3-isopropyl-phenyl)-propyl, 4-(4-methyl-pent-3-enyl)-cyclohex-3-ene-1-yl, 4-(2,6,6-trimethylcyclohex-2-en-1-yl)-2-butyl, 3-(4-tert-butylphenyl)-2-propyl, 2-(4-tert-butylphenyl)-ethyl, 3-(benzo[1,3]dioxol-5-yl)-2-propyl, 2,6-dimethyl-5-heptenyl, 3-(p-isopropyl-phenyl)-2-propyl, (3,7-dimethyl-oct6-enyloxy)-methyl, (5Z)-octa-1,5-dienyl, 1-nonenyl, 1-undecenyl, 2,6-dimethyl-hepta-1,5-dienyl, 2,6-dimethyl-octa-1,5-dienyl, or $R^2$=$R^4$ are methyl, and $R^3$=$R^5$ are pentyl, hexyl, heptyl, octyl, nonyl, 2-phenyl-ethyl, 4-methyl-pent-3-ene-1-yl, 4,8-dimethyl-nona-3,7-dien-1-yl, (2,6,6-trimethylcyclohex-1-ene-1-yl)-ethyl, (2,6,6-trimethylcyclohex-1-ene-2-yl)-ethyl, 2-(4-hydroxyphenyl)-ethyl, (1,3-benzodioxole-5-yl)-ethyl, or $R^2$=$R^4$ are ethyl, and $R^3$=$R^5$ are 5-methyl-hex-4-en-2-yl, or $R^2CHR^3$=$R^4CHR^5$ are 2-heptyl-cyclopentyl, 7-methyl-3,4-dihydro-2H-1,5-benzodioxepin-3-yl, 3-methyl-cyclopentadecyl, cyclopentadecyl, 5-cyclohexadecen-1-yl, 4-(1,1-dimethylpropyl)-cyclohexyl, 2-(2-methylethyl)-5-methyl-cyclohexyl, 2-(1-methylethyl)-5-methyl-cyclohexyl, 2-(butan-2-yl)-cyclohexyl, 3-(2-oxo-propyl)-2-pentyl-cyclopentyl, 2-pentyl-3-(methoxycarbonylmethyl)-cyclopentyl, and these compounds constitute another aspect of the present invention.

Since the compounds of formula I, upon exposure to light are cleaved and provide a ketone of formula II and aldehydes or ketones of formula III and IV, they permit the development of useful consumer products with enhanced fragrant properties, especially having long lasting pleasant odor. Therefore, the present invention also relates to the use of all compounds of formula I as precursors for fragrant compounds.

The compounds of formula I can be used in any product in which a prolonged and defined release of the above mentioned fragrant compounds is desired. Therefore, these compounds are especially useful in functional perfumery, in products which are exposed to (sun)light during or after application.

The compounds of formula I can act as fragrance precursors in functional and fine perfumery i.e. in fine fragrances, industrial, institutional, home and personal care products. Industrial, institutional and home cleaning products to which the compound of formula I can be added are all kinds of detergents, window cleaners, hard surface cleaners, all purpose cleaners and furniture polishes. The products can be liquids or solids, such as powders or tablets. Fabrics and surfaces treated with a product comprising a compound of formula I will diffuse a fresh and/or clean odor upon exposure to light much longer than when cleaned with a conventional cleaner. Fabrics or clothes washed with such detergents will release the aldehydes and ketones even after having been stored for weeks in a dark place, e.g. a wardrobe.

The compounds of the formula I are also useful for application in all kinds of body care products. Especially interesting products are hair care products, for example shampoos, conditioners and hairsprays and skin care products such as cosmetic products and especially sun protection products.

The above mentioned examples are of course only illustrative and non-limiting. Many other products to which the compound of formula I may be added include soaps, bath and shower gels, deodorants and even perfumes and colognes.

The compounds of formula I can be used alone or in combination with other fragrance ingredients, solvents or adjuvants known to those skilled in the art. Such ingredients are described, for example, in "Perfume and Flavor Chemicals", S. Arctander, Ed., Vol. I & II, Allured Publishing Corporation, Carol Stream, USA, 1994 and include fragrance compounds of natural or synthetic origin and essential oils.

The amounts in which the compounds of formula I are incorporated in the various above-mentioned products vary within a wide range. The amounts depend on the nature of the aldehydes and ketones to be released, the nature of the product to which the compounds of formula I are added and the desired olfactory effect. The amounts used also depend on the co-ingredients in a given composition when the compounds of formula I are used in admixture with perfuming co-ingredients, solvents or adjuvants. Typical concentrations are in the order of 0.01% to 5% by weight of the products.

The following non-limiting examples further illustrate the embodiments of the invention.

The following chemicals were obtained from commercial sources: 2,2-dimethoxy-2-phenylacetophenone, α,α-diethoxy-acetophenone, 2'-acetonaphthone, acetanisole, 4'-hydroxyacetophenone, 4'-(methylthio)-acetophenone, 3',4'-(methylendioxy)-acetophenone, 3',4'-dimethoxy-acetophenone, Fixolide®, 4'-(diethylamino)-acetophenone, 10-undecene-1-ol, 1-hexanol, β-citronellol, (−)-menthol.

The following alcohols are known in the literature and were prepared from their corresponding commercially available aldehyde or ketone by standard lithium alimunium hydride reduction: 2,6,10-trimethyl-undec-9-en-1-ol, 2,6-dimethyl-hept-5-en-1-ol, 2-methyl-undecan-1-ol, 3-(4-tert-butyl-phenyl)-2-methyl-propan-1-ol, 3-(3-isopropyl-phenyl)-butan-1-ol, (2,4-dimethyl-cyclohex-3-enyl)-methanol, 4-(2,6,6-trimethyl-cyclohex-1-enyl)-butan-2-ol.

NMR: values of coupling constants J are given in Hertz.

EXAMPLE 1

Preparation of Aroyl Formaldehyde Acetals

1. General Procedure for the Preparation of para-O-substituted Acetophenones

To a mechanically stirred mixture of 4'-hydroxyacetophenone (27.3 g, 0.2 mol), anhydrous potassium carbonate (33.2 g, 0.24 mol, 1.2 equiv.) and potassium iodide (3.2 g, 0.02 mol, 0.1 equiv.) in dimethylformamide (250 ml) was added dropwise the corresponding alkyl chloride or bromide (0.24 mol, 1.2 equiv.). Then, the mixture was heated at either 60° C. (for alkyl bromides) or 80° C. (for alkyl chlorides) for 6-16 h. The completion of the reaction was monitored by TLC or GLC. The off-white to beige reaction mixture was poured into ice/water (300 ml) and extracted with MTBE (2×250 ml). The organic phases were each washed with water (200 ml) and brine (100 ml), combined, dried ($Na_2SO_4$) and concentrated in vacuo to give the required product in usually quantitative yield.

1-(4-Propoxy-phenyl)-ethanone

Obtained as a very pale yellow oil according to the general procedure.

$^1$H-NMR (400 MHz, $CDCl_3$): 1.05 (t, 3H, J 7.5); 1.79-1.87 (m, 2H); 2.55 (s, 3H); 3.98 (t, 2H, J 7.5); 6.92 (apparent d, 2H); 7.92 (apparent d, 2H).IR ($v_{max}$, cm$^{-1}$, ATR): 1674s, 1599s, 1254s.MS [m/z (EI)]: 178 ($M^+$, 20%), 163 (18), 121 (100).

1-(4-Decyloxy-phenyl)-ethanone

Obtained as a white solid according to the general procedure.

mp 33-34° C. (EtOH).

$^1$H-NMR (400 MHz, $CDCl_3$): 0.88 (t, 3H, J 7.5); 1.23-1.38 (m, 12H); 1.40-1.50 (m, 2H); 1.74-1.83 (m, 2H); 2.54 (s, 3H); 4.00 (t, 2H, J 7.5); 6.91 (apparent d, 2H); 7.91 (apparent d, 2H).IR ($v_{max}$, cm$^{-1}$, ATR): 2921s, 2852m, 1675s, 1605m, 1311s.MS [m/z (EI)]: 276 ($M^+$, 28%), 261 (18), 137 (43), 121 (100).

1-(4-Octadecyloxy-phenyl)-ethanone

Obtained as a white solid according to the general procedure.

mp 69-70° C. (EtOH). $^1$H-NMR (400 MHz, $CDCl_3$): 0.88 (t, 3H, J 7.5); 1.23-1.38 (m, 28H); 1.40-1.49 (m, 2H); 1.75-1.84 (m, 2H); 2.55 (s, 3H); 4.01 (t, 2H, J 7.5); 6.92 (apparent d, 2H); 7.92 (apparent d, 2H).IR ($v_{max}$, cm$^{-1}$, ATR): 2920s, 2851S, 1676s, 1607m, 1256s.MS [m/z (EI)]: 388 ($M^+$, 14%), 373 (6), 137 (68), 121 (100).

1-[4-(2-Methoxy-ethoxy)-phenyl]-ethanone

Obtained as a very pale yellow oil according to the general procedure.

$^1$H-NMR (400 MHz, $CDCl_3$): 2.54 (s, 3H); 3.45 (s, 3H); 3.75-3.78 (m, 2H); 4.16-4.18 (m, 2H); 6.95 (apparent d, 2H); 7.92 (apparent d, 2H) IR ($v_{max}$, cm$^{-1}$, ATR): 1673s, 1600s, 1254s. MS [m/z (EI)]: 194 (M+, 40%), 179 (42), 121 (85), 59 (100).

2. General Procedures for the Preparation of Compounds of the Formula I

Method A:

To a stirred solution of the acetophenone derivative (either from 1. or from commercial source, 0.2 mol) in dimethylsulfoxide (300 ml) was added dropwise aqueous hydrobromic acid (47%, 70 ml, 0.6 mol, 3 equiv.) within 40 minutes, during which the reaction temperature rised to 45° C. The resulting pale yellow to pale brown, clear mixture was heated at 55° C. for 5-10 h. The expense of starting material was monitored by TLC. After the reaction was completed, the formed dimethyl sulfide was removed under reduced pressure (water aspirator) for 1 h at 55° C. The mixture was allowed to cool and poured into ice/water (600 ml), upon which the hydrated arylglyoxal precipitated. This was filtered off, washed with water (3×150 ml) and dried in vacuo. (In some cases, the arylglyoxal hydrate does not precipitate, but can be isolated by extraction with ethyl acetate).

The crude arylglyoxal hydrate was dissolved in ethanol (abs., 300 ml) and pyridinium toluene-4-sulfonate (2.5 g, 0.01 mol, max. 5 mol %) was added. The pale yellow to brown solution was heated to reflux and ethanol (approx. 250 ml) was distilled off. Fresh ethanol (abs. 250 ml) was added and the procedure repeated 4 to 9 times. The completion of the reaction was monitored by TLC. The rection mixture was reduced to dryness in vacuo to give the intermediate α,α-diethoxy-acetophenone derivative.

To an aliquot of this residue [1/10, containing the α,α-diethoxy-acetophenone derivative (<0.02 mol) and pyridinium toluene-4-sulfonate (>0.001 mol, >5 mol %); or the α,α-di(m)ethoxy-acetophenone derivative from commercial source or the α,α-dimethoxy-acetophenone derivative from the general procedure B (see below) together with pyridinium toluene-4-sulfonate (5 mol %)] was added the alcohol (derived from the corresponding aldehyde or ketone, 0.06 mol, 3 equiv.) and the resulting solution was heated at 100° C. for 6-36 h, depending on the nature of the starting materials. The completion of the reaction was monitored by TLC. After cooling, the resulting yellow to dark brown suspension was diluted with hexane (100 ml) and washed with water (2×50 ml) and brine (30 ml), dried ($Na_2SO_4$) and concentrated in vacuo. The excess alcohol was distilled off under reduced pressure (0.1 mbar) in a 'Kugelrohr' apparatus. The residue was diluted with hexane (10 ml) and treated with activated charcoal (1 to 3 g). The suspension was heated to reflux for 1 to 2 h, cooled and filtered through a plug of Celite® and concentrated in vacuo to afford the required Aroyl-Formaldehyde Acetal (generally >90% purity).

Method B:

A mixture of the acetophenone derivative (0.1 mol), diphenyl diselenide (16 g, 0.05 mol, 0.5 equiv.) and ammonium peroxydisulfate (68.5 g, 0.3 mol, 3 equiv.) in methanol (600 ml) was heated to reflux and stirred for 1 to 2 h. The completion of the reaction was monitored by TLC or GLC. Methanol was removed in vacuo and the yellow to brown residue taken up in water (200 ml). This was extracted with MTBE (2×200 ml) and the organic phases each washed with water (200 ml) and brine (100 ml), combined, dried ($Na_2SO_4$) and concentrated in vacuo. The crude product was filtered through a plug of silica and diphenyl diselenide was eluted with hexane (1000 to 2000 ml) and isolated (this could be recycled several times with only moderate loss). Further elution of the silica plug with either MTBE or ethyl acetate (depending on the nature of the product) and concentration of the filtrate in vacuo afforded the desired α,α-dimethoxy-acetophenone derivative in 75-80% yield. In some cases, when the product was dark yellow to brown, a charcoal treatment was adequat.

The trans-acetalisation was performed as descibed under method A.

3. Representative Selection of Compounds of Formula I.

1-Phenyl-2,2-bis-undec-10-enyloxy-ethanone

Obtained as a very pale yellow oil from 10-undecen-1-ol and commercial α,α-diethoxy-acetophenone according to method A.

$^1$H-NMR (400 MHz, $CDCl_3$): 1.20-1.38 (m, 24H); 1.55-1.63 (m, 4H); 2.02 (q, 4H, J 7); 3.55-3.59 (m, 2H); 3.66-3.70 (m, 4H); 4.92 (apparent d, 2H, J 9.5); 4.98 (apparent d, 2H, J 17); 5.22 (s, 1H); 5.80 (ddt, 2H, J 17, 9.5, 3); 7.43 (apparent t, 2H, J 7.5); 7.54 (apparent t, 1H, J 7.5); 8.16 (apparent d, 2H, J 7.5).IR ($v_{max}$, $cm^{-1}$, ATR): 3075w, 2925s, 2855m, 1689m, 1070s.MS [m/z (EI)]: 457 ([M+H]$^+$, 1%), 351 (10), 111 (21), 105 (14), 97 (77), 83 (56), 69 (100), 55 (45).UV [$\lambda_{max}$ in nm (ε), EtOH]: 283sh (1740), 248 (12930).

1-(4-Methoxy-phenyl)-2,2-bis-undec$^{-10}$-enyloxy-ethanone

Obtained as a very pale yellow oil from 10-undecen-1-ol and acetanisole according to method A.

$^1$H-NMR (400 MHz, $CDCl_3$): 1.20-1.39 (m, 24H); 1.56-1.64 (m, 4H); 2.02 (q, 4H, J 7); 3.53-3.58 (m, 2H); 3.65-3.69 (m, 2H); 3.86 (s, 3H); 4.92 (apparent d, 2H, J 9.5); 4.98 (apparent d, 2H, J 17); 5.17 (s, 1H); 5.80 (ddt, 2H, J 17, 9.5, 3); 6.91 (apparent d, 2H, J 9); 8.16 (apparent d, 2H, J 9).IR ($v_{max}$, $cm^{-1}$, ATR): 3078w, 2925s, 2854m, 1681m, 1600s, 1258s.MS [m/z (EI)]: 487 ([M+H]$^+$, 1%), 351 (71), 153 (44), 135 (74), 111 (75), 105 (14), 97 (100), 83 (93), 69 (83), 55 (87).UV [$\lambda_{max}$ in nm (ε), EtOH]: 284 (12500), 222 (8100).

2,2-Bis-phenethyloxy-1-(4-propoxy-phenyl)-ethanone

Obtained as a very pale yellow oil from phenethylalcohol and 1-(4-propoxy-phenyl)-ethanone according to method A.

$^1$H-NMR (400 MHz, $CDCl_3$): 1.04 (t, 3H, J 7); 1.77-1.88 (m, 2H); 2.86 (t, 4H, J 7); 3.68-3.75 (m, 2H); 3.78-3.85 (m, 2H); 3.96 (t, 2H, J 6.5); 5.20 (s, 1H); 6.83 (apparent d, 2H, J 9); 7.12-7.27 (m, 10H); 8.00 (apparent d, 2H, J 9). IR ($v_{max}$, $cm^{-1}$, ATR): 1678m, 1599s, 1064s. MS [m/z (EI)]: 418 (M$^+$, <1%), 255 (12), 163 (31), 121 (43), 105 (100), 91 (23). UV [$\lambda_{max}$ in nm (ε), EtOH]: 286 (17160).

2,2-Bis-(2-isopropyl-5-methyl-cyclohexyloxy)-1-(4-propoxy-phenyl)-ethanone

Obtained as a very pale yellow oil from (−)-menthol and 1-(4-propoxy-phenyl)-ethanone according to method A.

$^1$H-NMR (400 MHz, $CDCl_3$): 0.44 (d, 3H, J 7), 0.75 (d, 3H, J 7), 0.75-1.07 (m, 22H); 1.08-1.41 (m, 5H); 1.53-1.67 (m, 4H); 1.77-1.87 (m, 2H); 2.19-2.25 (m, 1H); 2.36-2.45 (m, 1H); 3.24 (td, 1H, J 10.5, 4); 3.49 (td, 1H, J 11, 4.5); 3.93 (t, 2H, J 6.5); 5.05 (s, 1H); 6.89 (apparent d, 2H, J 9); 8.21 (apparent, 2H, J 9). IR ($v_{max}$, $cm^{-1}$, ATR): 2954m, 2922m, 1677m, 1600s, 1256s, 1064s. MS [m/z (EI)]: 486 (M$^+$, <1%), 323 (3), 163 (28), 139 (85), 121 (19), 83 (100), 57 (40). UV [$\lambda_{max}$ in nm (ε), EtOH]: 285 (17920), 222 (10610).

2,2-Bis-[1-methyl-3-(2,6,6-trimethyl-cyclohex-1-enyl)-propoxy]-1-(4-propoxy-phenyl)-ethanone Obtained as mixture of diastereoisomers (a pale yellow oil) from racemic β-dihydroionone and 1-(4-propoxy-phenyl)-ethanone according to method A.

$^1$H-NMR (400 MHz, $CDCl_3$): 0.81-0.86 (m, 6H), 0.98-1.05 (m, 9H), 1.13 (m, 3H); 1.28-1.95 (m, 29H); 1.96-2.07 (m, 1H); 2.23-2.33 (m, 1H); 3.61-3.73 (m, 1H); 3.77-3.86 (m, 1H); 3.94-4.00 (m, 2H); 5.04, 5.06, 5.07 (3×s, 1H); 6.88 (apparent d, 2H, J 9); 8.26 (apparent d, 2H, J 9). IR($v_{max}$, $cm^{-1}$, ATR) 2928m, 1678m, 1600s, 1257s, 1022s. MS [m/z (EI)]: 566 (M$^+$, <1%), 403 (3), 179 (61), 163 (52) 137 (100), 123 (84), 109 (76), 95 (91), 81 (56). UV [$\lambda_{max}$ in nm (ε), EtOH]: 284 (16550).

1-(4-Decyloxy-phenyl)-2,2-bis-(3,7-dimethyl-oct-6-enyloxy)-ethanone

Obtained as a pale yellow oil from citronellol and 1-(4-decyloxy-phenyl)-ethanone according to method A.

$^1$H-NMR (400 MHz, $CDCl_3$): 0.83-0.91 (m, 9H); 1.08-1.19 (m, 2H); 1.20-1.40 (m, 14H); 1.40-1.48 (m, 4H); 1.50-1.71 (m, 4H); 1.57 (s, 6H); 1.66 (s, 6H); 1.83-1.94 (m, 2H); 1.95-2.04 (m, 4H); 3.55-3.62 (m, 2H); 3.68-3.75 (m, 2H); 4.00 (t, 2H, J 6.5); 5.05 (apparent t, 2H, J 7.5); 5.16 (s, 1H); 6.89 (apparent d, 2H, J 9); 8.14 (apparent d, 2H, J 9). IR ($v_{max}$, $cm^{-1}$, ATR): 2924s, 2855m, 1681m, 1600s, 1255s. MS [m/z (EI)]: 584 (M$^+$, <1%), 430 (1), 292 (2), 261 (8) 139 (38), 121 (23), 83 (100), 69 (72), 57 (41). UV [$\lambda_{max}$ in nm (ε), EtOH]: 286 (17210), 223 (9790).

2,2-Bis-[3-(4-tert-butyl-phenyl)-2-methyl-propoxy]-1-(4-octadecyloxy-phenyl)-ethanone Obtained as mixture of diastereoisomers (a pale brown solid) from 3-(4-tert-butyl-phenyl)-2-methyl-propan-1-ol and 1-(4-octadecyloxy-phenyl)-ethanone according to method A.

mp 40-42° C.

$^1$H-NMR (400 MHz, $CDCl_3$): 0.86-0.90 (m, 9H); 1.23-1.39 (m, 46H); 1.40-1.49 (m, 2H); 1.73-1.82 (m, 2H); 1.99-2.08 (m, 2H); 2.29-2.39 (m, 2H); 2.65-2.75 (m, 2H); 3.32-3.43 (m, 2H); 3.50-3.61 (m, 2H); 4.00 (t, 2H, J 6.5); 5.06, 5.09, 5.10 (3×s, 1H); 6.91 (apparent d, 2H, J 9); 7.03 (apparent t, 4H, J 9); 7.22-7.28 (m, 4H); 8.16-8.21 (m, 2H). IR ($v_{max}$, $cm^{-1}$, ATR): 2924s, 2853s, 1681m, 1600s, 1256s. MS [m/z (EI)]: 592 ([M-Lilial®]$^+$, <1%), 576 (2), 423 (1), 388 (7), 206 (18), 191 (97), 131 (68), 91 (57), 57 (100). UV [$\lambda_{max}$ in nm (ε), EtOH]: 286 (15850), 222 (24680).

2,2-Bis-(2,4-dimethyl-cyclohex-3-enylmethoxy)-1-(4-propoxy-phenyl)-ethanone

Obtained as mixture of diastereoisomers (a pale brown oil) from (2,4-dimethyl-cyclohex-3-enyl)-methanol and 1-(4-propoxy-phenyl)-ethanone according to method A.

$^1$H-NMR (400 MHz, $CDCl_3$): 0.87-1.01 (m, 6H); 1.04 (t, 3H, J 7); 1.34-1.48 (m, 4H); 1.62 (apparent s, 6H); 1.77-2.01 (m, 10H); 3.39-3.44 (m, 1H); 3.56-3.65 (m, 2H); 3.74-3.79 (m, 1H); 3.99 (t, 2H, J 6.5); 5.05-5.30 (m, 3H); 6.90 (apparent d, 2H, J 9); 8.14 (apparent d, 2H, J 9). IR ($v_{max}$ $cm^{-1}$, ATR): 2960m, 2924m, 2873m, 1680m, 1599s, 1257s. MS [m/z (EI)]: 454 (M$^+$, <1%), 315 (1), 291 (5), 163 (20), 151 (62), 123 (100), 81 (88), 67 (55), 57 (29). UV [$\lambda_{max}$ in nm (ε), EtOH]: 285 (17020), 222 (9390).

1-[4-(2-Methoxy-ethoxy)-phenyl]-2,2-bis-(2,6,10-trimethyl-undec-9-enyloxy)-ethanone Obtained as mixture of diastereoisomers (a pale brown oil) from 2,6,10-trimethyl-undec-9-en-1-ol and 1-[4-(2-methoxy-ethoxy)-phenyl]-ethanone according to method B.

¹H-NMR (400 MHz, CDCl₃): 0.84 (d, 6H, J 6.5); 0.88-0.91 (m, 6H); 0.98-1.45 (m, 18H); 1.59 (apparent s, 6H); 1.68 (apparent s, 6H); 1.70-1.78 (m, 2H); 1.86-2.04 (m, 4H); 3.29-3.34 (m, 1H); 3.37-3.50 (m, 2H); 3.44 (s, 3H); 3.53-3.59 (m, 1H); 3.75 (t, 2H, J 4.5); 4.17 (t, 2H, J 4.5); 5.04-5.13 (m, 3H); 6.94 (apparent d, 2H, J 9); 8.15 (apparent d, 2H, J 9). IR ($v_{max}$, cm⁻¹, ATR): 2924s, 2872m, 1681m, 1600s, 1293s. MS [m/z (EI)]: 615 ([M+H]⁺, <1%), 435 (13), 404 (8), 209 (20), 195 (18), 179 (40), 139 (75), 125 (76), 113 (86), 97 (85), 83 (100), 69 (93), 57 (88). UV [$\lambda_{max}$ in nm (6), EtOH]: 284 (12850), 221 (5970).

1-[4-(2-Methoxy-ethoxy)-phenyl]-2,2-bis-(2-methyl-undecyloxy)-ethanone

Obtained as mixture of diastereoisomers (a pale yellow oil) from 2-methyl-undecan-1-ol and 1-[4-(2-methoxy-ethoxy)-phenyl]-ethanone according to method A or B.

¹H-NMR (400 MHz, CDCl₃): 0.86-0.92 (m, 12H); 1.02-1.15 (m, 2H); 1.16-1.42 (m, 30H); 1.67-1.78 (m, 2H); 3.30 (dd, 1H, J 9, 6.5); 3.38-3.48 (m, 2H); 3.44 (s, 3H); 3.52-3.57 (m, 1H); 3.76 (dd, 2H, J 4.5, 3.5); 4.17 (dd, 2H, J 4.5, 3.5); 5.08, 5.09, 5.1 (3×s, 1H); 6.94 (apparent d, 2H, J 9); 8.15 (apparent d, 2H, J 9). IR ($v_{max}$, cm⁻¹, ATR): 2923s, 2854s, 1682m, 1601s, 1257s. MS [m/z (EI)]: 563 ([M+H]⁺, <1%), 383 (12), 209 (21), 179 (52), 169 (100), 127 (30), 121 (38), 113 (73), 99 (95), 85 (98), 71 (99), 57 (96), 43 (76). UV [$\lambda_{max}$ in nm (ϵ), EtOH]: 283 (15190), 222 (8670).

1-(4-Methylsulfanyl-phenyl)-2,2-bis-(2-methyl-undecyloxy)-ethanone

Obtained as mixture of diastereoisomers (a pale yellow oil) from 2-methyl-undecan-1-ol and 4'-(methylthio)-acetophenone according to method B.

¹H-NMR (400 MHz, CDCl₃): 0.84-0.94 (m, 12H); 1.05-1.17 (m, 2H); 1.17-1.43 (m, 30H); 1.69-1.78 (m, 2H); 2.76 (s, 3H); 3.34 (dd, 1H, J 9, 6.5); 3.39-3.47 (m, 1H); 3.48-3.56 (m, 1H); 3.58-3.64 (m, 1H); 5.06, 5.065, 5.07 (3×s, 1H); 7.72 (apparent d, 2H, J 8.5); 8.33 (apparent d, 2H, J 9). IR ($v_{max}$, cm⁻¹, ATR): 2923s, 2853m, 1694m, 1591w, 1053s. MS [m/z (EI)]: 533 ([M−H]⁻, 6%), 505 (12), 383 (10), 197 (17), 169 (100), 151 (41), 127 (30), 113 (69), 99 (84), 85 (85), 71 (83), 57 (77), 43 (71). UV [$\lambda_{max}$ in nm (ϵ), EtOH]: 271 (6320), 240 (9100).

2,2-Bis-(2,6-dimethyl-hept-5-enyloxy)-1-(3,5,5,6,8,8-hexamethyl-5,6,7,8-tetrahydro-naphthalen-2-yl)-ethanone Obtained as mixture of diastereoisomers (a yellow gum) from 2,6-dimethyl-hept-5-en-1-ol and 1-(3,5,5,6,8,8-hexamethyl-5,6,7,8-tetrahydro-naphthalen-2-yl)-ethanone according to method B.

¹H-NMR (400 MHz, CDCl₃): 0.89-0.92 (m, 6H); 0.99 (d, 3H, J 7); 1.07 (s, 3H); 1.07-1.19 (m, 2H); 1.26 (s, 3H); 1.31 (s, 3H); 1.40 (s, 3H); 1.36-1.49 (m, 3H); 1.56 (s, 6H); 1.58-1.81 (m, 4H); 1.65 (s, 6H); 1.83-2.04 (m, 4H); 2.50 (s, 3H); 3.34 (dd, 1H, J 9, 6.5); 3.40-3.49 (m, 2H); 3.50-3.57 (m, 1H); 5.01-5.07 (m, 3H); 7.18 (s, 1H); 8.14 (s, 1H). IR ($v_{max}$, cm⁻¹, ATR): 2964s, 2912m, 1679m, 1455m, 1053s. MS [m/z (EI)]: 538 (M⁺, <1%), 397 (1), 295 (2), 243 (34), 125 (75), 83 (47), 69 (100), 57 (53), 41 (33). UV [$\lambda_{max}$ in nm (ϵ), EtOH]: 298sh (1140), 264 (14250).

2,2-Bis-[3-(3-isopropyl-phenyl)-butoxy]-1-naphthalen-2-yl-ethanone

Obtained as mixture of diastereoisomers (a pale yellow gum) from 3-(3-isopropyl-phenyl)-butan-1-ol and 1-naphthalen-2-yl-ethanone according to method A.

¹H-NMR (400 MHz, CDCl₃): 1.03-1.27 (m, 18H); 1.83-1.92 (m, 4H); 2.73-2.91 (m, 4H); 3.41-3.53 (m, 2H); 3.55-3.72 (m, 2H); 5.17, 5.175, 5.18 (3×s, 1H); 6.88-7.03 (m, 6H); 7.11-7.18 (m, 2H); 7.50 (apparent t, 1H, J 7); 7.55 (apparent t, 1H, J 7); 7.82 (apparent d, 1H, J 8); 7.85 (apparent d, 1H, J 8.5); 7.96 (apparent d, 1H, J 8); 8.16 (apparent d, 1H, J 8.5); 8.80 (s, 1H). IR ($v_{max}$, cm⁻¹, ATR): 2958m, 1687m, 1487m, 1050s. MS [m/z (EI)]: 532 (<1%), 395 (21), 175 (86), 155 (24), 147 (57), 133 (100), 105 (47), 91 (67), 43 (34). UV [$\lambda_{max}$ in nm (ϵ), EtOH] 286/295 (4150), 252 (32530), 209 (32280).

2,2-Bis-(2-methyl-undecyloxy)-1,2-diphenyl-ethanone

Obtained as mixture of diastereoisomers (a pale yellow oil) from 2-methyl-undecan-1-ol and 2,2-dimethoxy-2-phenyl-acetophenone according to method A.

¹H-NMR (400 MHz, CDCl₃): 0.85-0.94 (m, 12H); 1.05-1.41 (m, 32H); 1.66-1.75 (m, 2H); 3.07-3.14 (m, 2H); 3.18-3.29 (m, 2H); 7.22-7.39 (m, 6H); 7.62 (apparent d, 2H, J 7.5); 8.02 (apparent d, 2H, J 7.5). IR ($v_{max}$, cm⁻¹, ATR): 2923s, 2853m, 1698m, 1448m, 1055s. MS [m/z (EI)]: 459 ([M−PhCO]⁺, 13%), 291 (43), 211 (23), 169 (76), 123 (100), 105 (75), 85 (78), 71 (83), 57 (88), 43 (77). UV [$\lambda_{max}$ in nm (ϵ), EtOH] 252 (12750).

1-(3,4-Dimethoxy-phenyl)-2,2-bis-(2-methyl-undecyloxy)-ethanone

Obtained as mixture of diastereoisomers (a yellow oil) from 2-methyl-undecan-1-ol and 1-(3,4-dimethoxy-phenyl)-ethanone according to method B.

¹H-NMR (400 MHz, CDCl₃): 0.84-0.92 (m, 12H); 1.05-1.17 (m, 2H); 1.17-1.43 (m, 30H); 1.69-1.78 (m, 2H); 3.33 (dd, 1H, J 9, 6.5); 3.42 (dd, 1H, J 9, 5.5); 3.45-3.52 (m, 1H); 3.54-3.59 (m, 1H); 3.93 (S, 3H); 3.94 (s, 3H); 5.09, 5.10, 5.11 (3×s, 1H); 6.94 (apparent d, 1H, J 8.5); 7.71 (d, 1H, J 2); 7.91 (dd, 1H, J 8.5, 2). IR ($v_{max}$, cm⁻¹, ATR): 2923s, 2854m, 1680m, 1595m, 1271s. MS [m/z (EI)]: 548 (M⁺, <1%), 383 (5), 195 (9), 169 (56), 165 (17), 113 (32), 99 (54), 85 (70), 71 (87), 57 (100), 43 (37). UV [$\lambda_{max}$ in nm (ϵ), EtOH]: 310 (8480), 279 (10280), 231 (15060).

1-Benzo[1,3]dioxol-5-yl-2,2-bis-[3-(4-tert-butyl-phenyl)-2-methyl-propoxy]-ethanone Obtained as mixture of diastereoisomers (a pale brown oil) from 3-(4-tert-butyl-phenyl)-2-methyl-propan-1-ol and 1-benzo[1,3]dioxol-5-yl-ethanone according to method B.

¹H-NMR (400 MHz, CDCl₃): 0.86-0.91 (m, 6H); 1.29 (m, 18H); 1.99-2.07 (m, 2H); 2.29-2.39 (m, 2H); 2.66-2.74 (m, 2H); 3.32-3.43 (m, 2H); 3.50-3.62 (m, 2H); 5.04, 5.05, 5.06 (3×s, 1H); 6.01 (s, 2H); 6.85 (apparent d, 1H, J 8.5); 7.04 (apparent t, 4H, J 9); 7.24-7.29 (m, 4H); 7.65-7.68 (m, 1H); 7.87-7.93 (m, 1H). IR ($v_{max}$, cm⁻¹, ATR): 2924m, 1681m, 1259s, 1039s. MS [m/z (EI)]: 572 (M⁺, <1%), 423 (12), 189 (95), 147 (94), 131 (20), 57 (100). UV [$\lambda_{max}$ in nm (ϵ), EtOH]: 314 (6870), 277 (5890), 219 (26220).

2,2-Bis-[3-(4-tert-butyl-phenyl)-2-methyl-propoxy]-1-(4-diethylamino-phenyl)-ethanone Obtained as mixture of diastereoisomers (an orange-brown oil) from 3-(4-tert-butyl-phenyl)-2-methyl-propan-1-ol and 1-(4-diethylamino-phenyl)-ethanone according to method B.

¹H-NMR (400 MHz, CDCl₃): 0.85-0.92 (m, 6H); 1.18-1.21 (m, 6H); 1.29 (s, 18H); 2.00-2.09 (m, 2H); 2.28-2.40 (m, 2H); 2.69-2.80 (m, 2H); 3.32-3.48 (m, 6H); 3.50-3.61 (m, 2H); 5.10, 5.12, 5.13 (3×s, 1H); 6.01 (s, 2H); 6.60-6.64 (m, 2H); 7.03-7.10 (m, 4H); 7.25-7.29 (m, 4H); 8.04-8.13 (m, 2H). IR ($v_{max}$, cm⁻¹, ATR): 2964m, 1665m, 1593s, 1196m, 1076m. MS [m/z (EI)]: 599 (M⁺, <1%), 423 (8), 395 (4), 189

(87), 147 (82), 131 (21), 57 (100). UV [λ$_{max}$ in nm (ε), EtOH]: 350 (9230), 245 (1600), 218sh (7060).

EXAMPLE 2

Photolysis of Compounds of Formula I (Aroyl-Formaldehyde Acetals) in Solution

Photolysis experiments were conducted on solutions (typical concentrations of compounds of formula I: 0.1% w/v in ethanol). The solutions were irradiated with a mercury lamp (150 W) in a borosilicate glass apparatus (Pyrex®) so as to limit the irradiation window to mainly the UVA and UVB spectrum (>300 nm). The alcoholic solution was irradiated for one to three hours and samples taken every 15 min to analyze the extent of the photolysis. The presence of the aryl ketone (II) and aldehyde/ketone (III) after photolysis in solutions (1 in ethanol abs.) was determined by using GLC retention times. Samples (2 μl) were injected (on column injection) without further dilution. Gas chromatography-flame ionisation detection (GC-FID) was carried out with a CE-Instruments TraceGC 2000 apparatus, using a Supelco Simplicity-1 fused silica capillary column (15 m, 0.53 mm id, 1.5 μm film, He carrier gas, 50 kPa). A typical temperature program consists of injecting at 100° C., heating at 30° C./min to 300° C. and keeping this temperature for 60 min. The retention times of the Aroyl-Formaldehyde Acetals (I) vary from 10 to 30 minutes. The results after 15 minutes of irradiation are given in table 1. The rate of cleavage was established according to chromophores (II): Fixolide®>deoxybenzoin~p-alkoxy-acetophenones~p-methylthio-acetophenone>p-(2-methoxy-ethoxy)-acetophenones>acetophenone>>m,p-dialkoxy-acetophenones>>2'-acetonaphthone; and according to the aldehyde/ketone(III): aldehydes>>ketones. The low recovery of fragrance [generally below 2% of (II) and below 15% of (III) at complete conversion] is due to the instability towards free radicals which are constantly generated under these severe irradiation conditions.

TABLE 1

Release of aryl ketones (II) and aldehydes/ketones (III) from Aroyl-Formaldehyde Acetals (I) in solution upon 15 minutes of irradiation

| Aroyl-Formaldehyde Acetal (I) | Aryl ketone (II) | Aldehyde/Ketone (III) | unreacted (I) |
|---|---|---|---|
| 1 | Fixolide® <0.1% | Lilial® 3.0% | 1.9% |
| 2 | Oranger Crystals® <0.1% | Lilial® 1.4% | 94.9% |
| 3 | Acetophenone 1.6% | Lilial® 13.4% | 34.5% |
| 4 | Acetanisole <0.1% | Lilial® 12.2% | 12.5% |

TABLE 1-continued

Release of aryl ketones (II) and aldehydes/ketones (III) from Aroyl-Formaldehyde Acetals (I) in solution upon 15 minutes of irradiation

| Aroyl-Formaldehyde Acetal (I) | Aryl ketone (II) | Aldehyde/ Ketone (III) | unreacted (I) |
|---|---|---|---|
| 5 | <0.1% | (−)-Menthone 9.4% | 33.5% |
| 6 | <0.1% | Lilial ® 13.8% | 12.0% |
| 7 | <0.1% | Lilial ® 8.1% | 28.2% |
| 8 | <0.1% | Lilial ® 8.1% | 12.7% |
| 9 | <0.1% | Lilial ® 4.3% | 71.4% |

TABLE 1-continued

Release of aryl ketones (II) and
aldehydes/ketones (III) from Aroyl-Formaldehyde Acetals
(I) in solution upon 15 minutes of irradiation

| Aroyl-Formaldehyde Acetal (I) | Aryl ketone (II) | Aldehyde/ Ketone (III) | unreacted (I) |
|---|---|---|---|
| 10 | <0.1% | Lilial ® 1.1% | 9% |
| 11 | <0.1% | Lilial ® 0.8% | 95.9% |

EXAMPLE 3

Photorelease Assays on Fabric: Spray Tests 1 g of an approximately 0.2% Aroyl-Formaldehyde Acetals (I) solution in ethanol was evenly sprayed on a Terry towel (white cotton towel, 25 cm×25 cm, 45 g), corresponding to 45-75 µg/g cotton. The sprayed towels were allowed to dry in a dark and odorless place. When dry, a first towel was irradiated for a few seconds up to a few minutes with a tanning lamp (Osram Ultra-Vitalux®, 300 W; at a distance of 50 cm, the light has approximately six to seven times the effect of the natural sunlight at noon on a sea-side mid-summer day or an energy of 1.9 mW/cm$^2$). A second towel was exposed for several minutes upto one hour to natural western European winter sun light behind an ordinary glass window (0.1-0.2 mW/cm$^2$). The evaluation was done by a trained panel of perfumers before and after light exposure. Before irradiation, the towels were judged to be odorless. The results after irradiation are summarized in table 2.

TABLE 2

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 1 | [structure] | Fioxolide ® | | Lilial ® | | +++ | ++ |
| | | +++ | ++ | ++ | + | | |
| 2 | [structure] | Fixolide ® | | Melonal ® | | +++ | ++ |
| | | +++ | ++ | +++ | + | | |
| 3 | [structure] | Oranger Crystals ® | | Lilial ® | | ++ | 0 |
| | | +++ | ++ | ++ | + | | |
| | | ++ | 0 | ++ | 0 | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/ Ketone (III) | | | |
| | | art. light | nat. light | art. light | nat. light | art. light | nat. light |
| 4 | [structure] | Oranger Crystals ® | 0 | Citronellal | 0 | ++ | 0 |
| 5 | [structure] | ++ Oranger Crystals ® | 0 | ++ Florhydral ® | + | + | 0 |
| 6 | [structure] | ++ Oranger Crystals ® | 0 | + 10-Undecenal | 0 | ++ | 0 |
| 4 | [structure] | ++ Acetanisole | 0 | ++ Lilial ® | 0 | +++ | ++ |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 5 | [structure: 4-methoxyphenyl aroyl formaldehyde acetal with two citronellyl groups] | +++ Acetanisole | ++ Acetanisole | +++ Citronellal | ++ Citronellal | +++ | ++ |
| 6 | [structure: 4-methoxyphenyl aroyl formaldehyde acetal with two 3-isopropylphenyl-containing groups] | +++ Acetanisole | ++ Acetanisole | +++ Florhydral ® | ++ Florhydral ® | ++ | + |
| 7 | [structure: 4-methoxyphenyl aroyl formaldehyde acetal with two 10-undecenyl groups] | +++ Acetanisole | ++ Acetanisole | ++ 10-Undecenal | + 10-Undecenal | +++ | ++ |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 8 | [structure] | no fragrance ingredient | | +++ Lilial® | ++ | +++ | ++ |
| 9 | [structure] | no fragrance ingredient | | +++ 2-Methyl-undecanal | ++ | +++ | +++ |
| 10 | [structure] | no fragrance ingredient | | +++ Phenyl-acetaldehyde | ++ | +++ | +++ |
| 11 | [structure] | no fragrance ingredient | | +++ Cyclal C® | ++ | +++ | + |
| | | | | +++ | + | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 12 | [structure] | no fragrance ingredient | | Adoxal ® | | ++ | + |
| 13 | [structure] | no fragrance ingredient | | ++ (−)-Menthone | + | ++ | + |
| 14 | [structure] | no fragrance ingredient | | ++ β-Dihydro-ionone | + | ++ | 0 |
| | | | | ++ | 0 | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | | | Global appreciation* | |
|---|---|---|---|---|---|---|---|---|---|
| | | Aryl ketone (II) | | Aldehyde/ Ketone (III) | | | | | |
| | | art. light | nat. light | art. light | | nat. light | | art. light | nat. light |
| 15 | [structure] | no fragrance ingredient | | +++ Lilial ® | | ++ | | +++ | ++ |
| 16 | [structure] | no fragrance ingredient | | +++ 2-Methyl-un- decanal | | +++ | | +++ | +++ |
| 17 | [structure] | no fragrance ingredient | | +++ Cyclal C ® | | + | | +++ | + |
| 18 | [structure] | no fragrance ingredient | | +++ Adoxal ® | + ++ | + | + | ++ | + |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 19 | [structure] | no fragrance ingredient | | +++ Citronellal | ++ | +++ | ++ |
| 20 | [structure] | no fragrance ingredient | | +++ 10-Undecenal | ++ | +++ | ++ |
| 21 | [structure] | no fragrance ingredient | | +++ Lilial® | ++ | +++ | ++ |
| 22 | [structure] | no fragrance ingredient | | +++ Citronellal | ++ | +++ | ++ |
| | | | | +++ | ++ | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 23 | [structure] | no fragrance ingredient | | Florhydral ® | | + | 0 |
| 24 | [structure] | no fragrance ingredient | | 10-Undecenal +++ | + | 0 +++ | ++ |
| 25 | [structure] | Acetophenone ++ | + | Lilial ® ++ | + | ++ | + |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | | | Global appreciation* | |
|---|---|---|---|---|---|---|---|---|---|
| | | Aryl ketone (II) | | Aldehyde/Ketone (III) | | | | | |
| | | art. light | nat. light | art. light | nat. light | | | art. light | nat. light |
| 26 | [structure] | ++ Acetanisole | + Acetanisole | ++ Citronellal | + Citronellal | | | ++ | + |
| 27 | [structure] | ++ Acetanisole | + Acetanisole | ++ 10-Undecenal | + 10-Undecenal | | | ++ | + |
| 28 | [structure] | ++ no fragrance ingredient | + no fragrance ingredient | ++ Hexanal | + Hexanal | | | ++ | + |
| 29 | [structure] | ++ no fragrance ingredient | no fragrance ingredient | ++ 2-Methyl-undecanal | + 2-Methyl-undecanal | | | +++ | +++ |
| | | | | +++ | ++ | | | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/ Ketone (III) | | | |
| | | art. light | nat. light | art. light | nat. light | art. light | nat. light |
| 30 | (structure) | no fragrance ingredient | | Lilial ® ++ | Lilial ® + | ++ | + |
| 31 | (structure) | no fragrance ingredient | | Lilial ® ++ | Lilial ® + | ++ | + |
| 32 | (structure) | no fragrance ingredient | | 2-Methyl-un-decanal +++ | 2-Methyl-un-decanal + | +++ | + |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/ Ketone (III) | | | |
| | | art. light | nat. light | art. light | nat. light | art. light | nat. light |
| 33 | [structure] | no fragrance ingredient | | +++ Lilial ® | ++ | +++ | ++ |
| 34 | [structure] | no fragrance ingredient | | +++ 2-Methyl-undecanal | ++ | +++ | +++ |
| 35 | [structure] | no fragrance ingredient | | +++ Phenyl-acetaldehyde | +++ | ++ | + |
| 36 | [structure] | no fragrance ingredient | | ++ Cyclal C ® | ++ | ++ | + |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 37 | [structure: 3,4-dimethoxyphenyl aroyl acetal with two 2-methyl-3-(4-tert-butylphenyl)propyl groups] | no fragrance ingredient | | ++ Lilial® | + | +++ | ++ |
| 38 | [structure: 3,4-dimethoxyphenyl aroyl acetal with two 2-methylundecyl groups] | no fragrance ingredient | | +++ 2-Methyl-undecanal | ++ | +++ | ++ |
| 39 | [structure: 3,4-dimethoxyphenyl aroyl acetal with two 2-phenylethyl groups] | no fragrance ingredient | | +++ Phenyl-acetaldehyde | ++ | ++ | + |
| | | | | ++ | + | | |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/Ketone (III) | | | |
| | | art. light | nat. light | art. light | nat. light | art. light | nat. light |
| 40 | [structure] | no fragrance ingredient | | Cyclal C ® ++ | Cyclal C ® + | ++ | + |
| 41 | [structure] | no fragrance ingredient | | Lilial ® ++ | Lilial ® + | + | 0 |
| 42 | [structure] | | | Lilial ® + | Lilial ® 0 | +++ | +++ |

TABLE 2-continued

Release of aryl ketones (II) and aldehydes/ketones (III) from Aroyl-Formaldehyde Acetals (I) on fabric upon irradiation with a tanning lamp.

| | Aroyl-Formaldehyde Acetal (I) | Fragrance Target (perception)* | | | | Global appreciation* | |
|---|---|---|---|---|---|---|---|
| | | Aryl ketone (II) | | Aldehyde/ Ketone (III) | | | |
| | | art. light | nat. light | art. light | nat. light | art. light | nat. light |
| 43 | [structure: aroyl-formaldehyde acetal with para-pivaloylamino phenyl ketone and two branched C12 alkoxy chains] | | | Aldehyde C12MNA | +++ | +++ | |

*0: very weak, +: weak, ++: medium, +++: strong

EXAMPLE 4

Stability Tests

Aroyl-Formaldehyde Acetals (I) were incubated in aqueous buffer solutions of pH 2.5, pH 7 and pH 9.5 for 24 h at 37° C. and were found to be stable in acida (pH<4), basic (pH>9) and neutral (pH 4-9) media. The results are summarized in table 3.

TABLE 2

Stability of Aroyl-Formaldehyde Acetals (I) under different pHs

| Aroyl-Formaldehyde Acetal (I) | pH 2.5 | pH 7 | pH 9.5 |
|---|---|---|---|
| 1 | stable | stable | stable |
| 2 | stable | stable | stable |

EXAMPLE 5

Preparation of an O/W Sunscreen Lotion UV-B and UV-A:
Sunscreen lotion containing 0.5% of perfume comprising one or more compounds of formula I of Example 1.

Recipe:

| Ingredients | % |
|---|---|
| Part A | |
| Octyl methoxycinnamate | 2.0 |
| 4-tert-butyl-4'methoxydibenzoyl methane | 3.0 |
| Isostearyl neopentanoate | 4.0 |
| Coco-caprylate/caprate | 12.0 |
| Diethyleneglycol monostearate | 0.25 |
| Cetylalcohol | 1.0 |
| Methyl-propylparabene | 0.25 |
| EDTA-sodium salt | 0.1 |
| Diethanolamine cetylphosphate | 1.0 |
| Perfume | 0.5 |
| Part B | |
| Acrylate C10-C30 Alkylacrylate | 20.0 |
| water | 50.1 |
| 1,2-Propanediol | 5.0 |
| Potassium hydroxide | 0.8 |

Process: Part A was heated in a reactor to 85° C. Part B was slowly added within 10 min. The emulsion was then cooled and degassed.

EXAMPLE 6

Fabric softeners (otherwise known as rinse conditioners) containing 0.5-0.7% perfume comprising one or more compounds of formula I of Example 1.

a) Fabric Softener of the Ester Quat Type (4× Concentrate)

| Ingredients | % |
|---|---|
| PHASE A | |
| WATER | 77.78 |
| aqueous MgCl$_2$ (sat. soln.) | 1.0 |
| PHASE B | |
| REWOQUAT WE 18 | 15.0 |
| GENAPOL O 100 | 2.0 |
| ANTIFOAM DB 31 | 0.5 |
| PHASE C | |
| ISOPROPYL ALCOHOL | 3.0 |
| PRESERVATIVE | 0.02 |
| PERFUME* | 0.7 |

PROCESS: While stirring and heating to 65° C., mix phase A, then phase B preheated to 65° C. After cooling to room temperature, add phase C. The pH value of the finished product is 2.60. Perfume*: one ore more of the compounds of formula I of Example 1 may be any part of this 0.7%.

b) Fabric Softener of the Ester Quat Type (1× Concentrate):

| Ingredients | % |
| --- | --- |
| PHASE A | |
| WATER | 92.85 |
| PHASE B | |
| REWOQUAT WE 18 | 6.0 |
| DOBANOL 25-9 | 0.5 |
| ANTIFOAM DB 31 | 0.1 |
| PHASE C | |
| MYACIDE BT 30 | 0.03 |
| PROXEL GXL | 0.02 |
| PERFUME* | 0.5 |

PROCESS: While stirring and heating to 65° C., mix phase A, then phase B preheated to 65° C. After cooling to room temperature, add phase C. The pH value of the finished product is 3.50. Perfume*: compounds of formula I of Example 1 may be any part of this 0.5%.

EXAMPLE 7

Heavy duty detergents containing perfume comprising one or more compounds of formula I of Example 1.

a) Heavy Duty Liquid Detergent (Regular)

| Ingredients | % |
| --- | --- |
| SURFACTANTS | 21.5 |
| AS/AEOS | 9.5 |
| SOAPS/FATTY ACIDS | 7.1 |
| NON-IONICS-AEO | 3.1 |
| NON-IONICS-FAGA | 1.8 |
| SODIUM CHLORIDE | 1.6 |
| BORAX | 1.7 |
| SODIUM CIT/CITRIC ACID | 1.2 |
| PHOSPHONATES | 0.3 |
| WATER | 47.5 |
| ETHANOL | 0.6 |
| MPG | 3.4 |
| PERFUME* | 0.7 | b) Heavy Duty Detergent Powder (Regular)

| Ingredients | % |
| --- | --- |
| SURFACTANTS | 12.1 |
| LAS/PS | 4.0 |
| SOAPS/FATTY ACIDS | 4.3 |
| NON-IONICS-AEO | 3.1 |
| P-P | 2.6 |
| STPP | 17.3 |
| SODIUM SULPHATE | 21.3 |
| SODIUM CARBONATE | 15.3 |
| SODIUM CHLORIDE | 1.1 |
| SODIUM SILICATE | 5.3 |
| ZEOLITES | 2.1 |
| POLYMERS - PCA | 2.1 |
| PERBORATES (SPT) | 8.9 |
| PERFUME* | 0.5 |

*One or more compounds of formula I of Example 1 may be any part of the PERFUME.

The invention claimed is:

1. A process for making a ketone of the formula II,

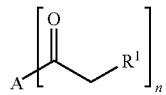

an aldehyde or ketone of the formula III comprising up to 20 carbon atoms, and

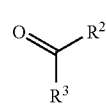

an aldehyde or ketone of the formula IV comprising up to 20 carbon atoms,

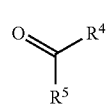

wherein

A is an aromatic or a heteroaromatic ring; or

A is an aromatic or heteroaromatic ring substituted with one or more residues selected from the group of alkyl, aryl, aralkyl, alkenyl, alkynyl, —OH, —O-alkyl, -alkoxyalkoxy, —O-aralkyl, —O-aryl, —O-acyl, —$NO_2$, —$NH_2$, —NH-alkyl, —N(alkyl)$_2$, —NH-acyl, —N(acyl)$_2$, —CN, —SH, —S-alkyl, —S-aryl and a halogen atom, selected from fluorine, chlorine or bromine; or A is an aromatic or heteroaromatic ring bearing a residue that together with the carbon atoms to which it is attached forms an aromatic or alicyclic ring, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues, $R^1$ represents hydrogen, alkyl, alkenyl, alkynyl, acyl or aryl residues, and said residues may comprise one or more oxygen atom(s), $R^2$, $R^3$, $R^4$, $R^5$ represent independently hydrogen, alkyl, alkenyl, alkynyl, cycloalkyl, cycloalkenyl or aromatic residues, and said residues may comprise one or more oxygen atom(s), $R^2$ and $R^3$ together with the carbon atom to which they are attached may form a 4 to 18 membered carbocyclic ring optionally substituted by an alkyl, alkenyl or alkynyl residue having up to 10 carbon atoms, and the ring and residues may comprise one or more oxygen atom(s), $R^4$ and $R^5$ together with the carbon atom to which they are attached may form a 4 to 18 membered carbocyclic ring optionally substituted by an alkyl, alkenyl or alkynyl residue having up to 10 carbon atoms, and the ring and residues may comprise one or more oxygen atom(s), and n is an integer from 1 to 3, which comprises subjecting to a photoreaction a compound of formula I

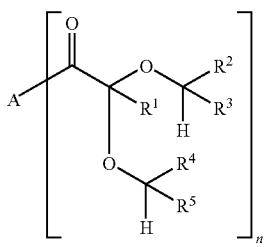

wherein A, $R^1$, $R^2$, $R^3$, $R^4$, $R^5$ and n are as defined above.

2. A process according to claim 1 wherein A is phenyl; or
A is phenyl substituted with one or more residues selected from the group of alkyl, aryl, aralkyl, alkenyl, alkynyl, —OH, —O-alkyl, -alkoxyalkoxy, —O-aralkyl, —O-aryl, —O-acyl, —NO₂, —NH₂, —NH-alkyl, —N(alkyl)₂, —NH-acyl, —N(acyl)₂, —CN, —SH, —S-alkyl, —S-aryl and a halogen atom, selected from fluorine, chlorine or bromine; or
A is phenyl bearing a residue that together with the carbon atoms to which it is attached forms an aromatic or alicyclic ring, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues.

3. A process according to claim 1, wherein n=1, $R^2$ and $R^4$ are independently an alkyl, alkenyl, alkynyl residue having 5 to 17 carbon atoms and $R^3$ and $R^5$ are H.

4. A process according to claim 1 wherein n=1, $R^2$ and $R^4$ are independently the residue of cyclic or acyclic terpene or the residue of a terpenoic aldehyde having 4 to 15 carbon atoms and $R^3$ and $R^5$ are H.

5. A process according to claim 1, wherein n=1, $R^2$ and $R^4$ are independently cycloalkyl, cycloalkenyl residues having 4 to 15 carbon atoms, and $R^3$ and $R^5$ are H.

6. A process according to claim 1, wherein n=1, $R^2$ and $R^4$ are independently aromatic residues having 4 to 15 carbon atoms, and $R^3$ and $R^5$ are H.

7. A process according to claim 1, wherein n=1, $R^2$ and $R^3$ are alkyl, alkenyl, alkynyl residues having together 5 to 17 carbon atoms, and $R^4$ and $R^5$ are alkyl, alkenyl, alkynyl residues having together 5 to 17 carbon atoms.

8. A process according to claim 1, wherein n=1, and $R^2$, $R^3$, $R^4$ and $R^5$ are the residues of cyclic or acyclic terpene or of a terpenoic ketone having 4 to 15 carbon atoms.

9. A process according to claim 1, wherein n=1, and $R^2$, $R^3$, $R^4$ and $R^5$ are the residues of cycloaliphatic ketones having 8 to 18 carbon atoms.

10. A process according to claim 1, wherein n=1, and $R^2$, $R^3$, $R^4$ and $R^5$ are the residues of araliphatic ketones having 8 to 18 carbon atoms.

11. A process according to claim 1, wherein n=1 and $R^1$=H.

12. A process according to claim 1, wherein n=1 and $R^1$ represents a linear or branched alkyl, alkenyl, aralkyl or aryl comprising 1 to 20 carbon atoms.

13. A process according to claim 12 wherein A is phenyl; or
A is phenyl substituted with one or more residues selected from the group of alkyl, aryl, aralkyl, alkenyl, alkynyl, —OH, —O-alkyl, -alkoxyalkoxy, —O-aralkyl, —O-aryl, —O-acyl, —NO₂, —NH₂, —NH-alkyl, —N(alkyl)₂, —NH-acyl, —N(acyl)₂, —CN, —SH, —S-alkyl, —S-aryl and a halogen atom, selected from fluorine, chlorine or bromine; or
A is phenyl bearing a residue that together with the carbon atoms to which it is attached forms an aromatic or alicyclic ring, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues.

14. A process according to claim 12, wherein $R^2$ and $R^4$ are independently an alkyl, alkenyl, alkynyl residue having 5 to 17 carbon atoms and $R^3$ and $R^5$ are H.

15. A process according to claim 12, wherein $R^2$ and $R^4$ are independently the residue of cyclic or acyclic terpene or the residue of a terpenoic aldehyde having 4 to 15 carbon atoms and $R^3$ and $R^5$ are H.

16. A process according to claims 12, wherein $R^2$ and $R^4$ are independently cycloalkyl, cycloalkenyl residues having 4 to 15 carbon atoms, and $R^3$ and $R^5$ are H.

17. A process according to claim 12, wherein $R^2$ and $R^4$ are independently aromatic residues having 4 to 15 carbon atoms, and $R^3$ and $R^5$ are H.

18. A process according to claim 12, wherein $R^2$ and $R^3$ are alkyl, alkenyl, alkynyl residues having together 5 to 17 carbon atoms, and $R^4$ and $R^5$ are alkyl, alkenyl, alkynyl residues having together 5 to 17 carbon atoms.

19. A process according to claim 12, wherein $R^2$, $R^3$, $R^4$ and $R^5$ are the residues of cyclic or acyclic terpene or of a terpenoic ketone having 4 to 15 carbon atoms.

20. A process according to claim 12, wherein $R^2$, $R^3$, $R^4$ and $R^5$ are the residues of cycloaliphatic ketones having 8 to 18 carbon atoms.

21. A process according to claim 12, wherein $R^2$, $R^3$, $R^4$ and $R^5$ are the residues of araliphatic ketones having 8 to 18 carbon atoms.

22. A process according to claim 1, wherein n=1, $R^1$=H,
A is an aromatic ring; or
A is an aromatic ring substituted with one or more residues selected from the group of alkyl, alkenyl, alkynyl, and alkoxy; or
A is an aromatic ring bearing a residue that together with the carbon atoms to which it is attached forms an aromatic or alicyclic ring, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues.

23. A process according to claim 22, wherein $R^2$ and $R^4$ are independently an alkyl, alkenyl, alkynyl residue having 5 to 17 carbon atoms and $R^3$ and $R^5$ are H.

24. A process according to claim 22, wherein $R^2$ and $R^4$ are independently the residue of cyclic or acyclic terpene or the residue of a terpenoic aldehyde having 4 to 15 carbon atoms and $R^3$ and $R^5$ are H.

25. A process according to claim 22, wherein $R^2$ and $R^4$ are independently cycloalkyl, cycloalkenyl residues having 4 to 15 carbon atoms, and $R^3$ and $R^5$ are H.

26. A process according to claim 22, wherein $R^2$ and $R^4$ are independently aromatic residues having 4 to 15 carbon atoms, and $R^3$ and $R^5$ are H.

27. A process according to claim 22, wherein $R^2$ and $R^3$ are alkyl, alkenyl, alkynyl residues having together 5 to 17 carbon atoms, and $R^4$ and $R^5$ are alkyl, alkenyl, alkynyl residues having together 5 to 17 carbon atoms.

28. A process according to claim 22, wherein $R^2$, $R^3$, $R^4$ and $R^5$ are the residues of cyclic or acyclic terpene or of a terpenoic ketone having 4 to 15 carbon atoms.

29. A process according to claim 22, wherein $R^2$, $R^3$, $R^4$ and $R^5$ are the residues of cycloaliphatic ketones having 8 to 18 carbon atoms.

30. A process according to claim 22, wherein $R^2$, $R^3$, $R^4$ and $R^5$ are the residues of araliphatic ketones having 8 to 18 carbon atoms.

31. A process according to claim 1, wherein n=1, $R^1$=H, and
  A is a heteroaromatic; or
  A is an aromatic or heteroaromatic ring substituted with one or more residues selected from the group —OH, —O-alkyl, -alkoxyalkoxy, —O-aralkyl, —O-aryl, —O-acyl, —NO$_2$, —NH$_2$, —NH-alkyl, —N(alkyl)$_2$, —NH-acyl, —N(acyl)$_2$, —SH, —S-alkyl, —S-aryl; or
  A is an aromatic or heteroaromatic ring bearing a residue that together with the carbon atoms to which it is attached forms an aromatic or alicyclic ring, or an aromatic or alicyclic ring bearing one or more heteroatoms selected from oxygen, nitrogen or sulphur, which aromatic or alicyclic ring may be substituted with one or more residues selected from the group of alkyl, alkenyl, and alkynyl residues.

32. A process according to claim 31, wherein $R^2$ and $R^4$ are independently an alkyl, alkenyl, alkynyl residue having 5 to 17 carbon atoms and $R^3$ and $R^5$ are H.

33. A process according to claim 31, wherein n=1, $R^2$ and $R^4$ are independently the residue of cyclic or acyclic terpene or the residue of a terpenoic aldehyde having 4 to 15 carbon atoms and $R^3$ and $R^5$ are H.

34. A process according to claim 31, wherein $R^2$ and $R^4$ are independently cycloalkyl, cycloalkenyl residues having 4 to 15 carbon atoms, and $R^3$ and $R^5$ are H.

35. A process according to claim 31, wherein $R^2$ and $R^4$ are independently aromatic residues having 4 to 15 carbon atoms, and $R^3$ and $R^5$ are H.

36. A process according to claim 31, wherein $R^2$ and $R^3$ are alkyl, alkenyl, alkynyl residues having together 5 to 17 carbon atoms, and $R^4$ and $R^5$ are alkyl, alkenyl, alkynyl residues having together 5 to 17 carbon atoms.

37. A process according to claim 31, wherein $R^2$, $R^3$, $R^4$ and $R^5$ are the residues of cyclic or acyclic terpene or of a terpenoic ketone having 4 to 15 carbon atoms.

38. A process according to claim 31, wherein $R^2$, $R^3$, $R^4$ and $R^5$ are the residues of cycloaliphatic ketones having 8 to 18 carbon atoms.

39. A process according to claim 31, wherein $R^2$, $R^3$, $R^4$ and $R^5$ are the residues of araliphatic ketones having 8 to 18 carbon atoms.

40. A process according to claim 1, wherein $R^2$ and $R^4$ are the same, and $R^3$ and $R^5$ are the same.

41. A compound of formula I

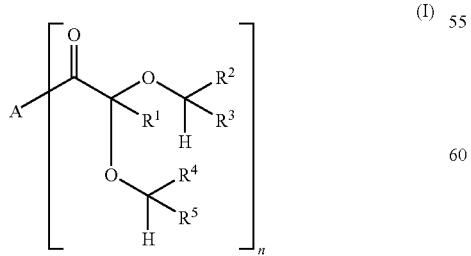

wherein n is 1,
$R^1$ is H, methyl, phenyl,

A is 6-tert-butyl-1,1-dimethyl-indan-4-yl, 2,4-dimethylphenyl, 3,5,5,6,8,8-hexamethyl-5,6,7,8-tetrahydro-naphthalen-2-yl, 5,6,7,8-tetrahydro-2-naphthalenyl, 1,1,2,3,3-pentamethyl-indan-5-yl, 2-naphthalenyl, 1,1,2,3,3,6-hexamethyl-indan-5-yl, 1,1,2,6-tetra-methyl-3-(1-methylethyl)-indan-5-yl, 3,5,5,8,8-pentamethyl-5,6,7,8-tetrahydro-naphthalen-2-yl, 3-ethyl-5,5,8,8-tetramethyl-5,6,7,8-tetrahydro-naphthalen-2-yl, 4-alkoxy-phenyl, 4-dialkylamino-phenyl, 4-acylamino-phenyl, 4-diacylamino-phenyl, 3,4-(methylenedioxy)-phenyl, 3,4-dialkoxy-phenyl, 4-(2-methoxyethoxy)-phenyl, 3,4-di-(2-methoxyethoxy)-phenyl, 4-[2-(2-methoxyethoxy)-ethoxy]-phenyl, 3,4-di-[2-(2-methoxyethoxy)-ethoxy]-phenyl, 2,3-dihydro-benzo[1,4]dioxin-6-yl, $R^2$ and $R^4$ are hydrogen, and $R^3$=$R^5$ are 6,10-dimethylundec-9-ene-2-yl, 2,4-dimethyl-cyclohex-3-ene-1-yl, 1,3,5-trimethyl-cyclohex-1-ene-4-yl, 4-(4-hydroxy-4-methyl-pentyl)-cyclohex-3-ene-1-yl, pent-1-enyl, hexyl, 6-methyl-hept-5-ene-2-yl, nonyl, 2-decyl, 9-decenyl, decyl, undecyl, 2-undecyl, heptyl, octyl, 8-decenyl, 1-phenyl-ethyl, (4-methyl-phenyl)-methyl, 2,6-dimethyl-heptyl, 2,6,10-trimethyl-undeca-5,9-dienyl, 2,6-dimethyl-6-hydroxy-heptyl, 2-(3-isopropyl-phenyl)-propyl, 4-(4-methyl-pent-3-enyl)-cyclohex-3-ene-1-yl, 4-(2,6,6-trimethylcyclohex-2-en-1-yl)-2-butyl, 3-(4-tert-butylphenyl)-2-propyl, 2-(4-tert-butylphenyl)-ethyl, 3-(benzo[1,3]dioxol-5-yl)-2-propyl, 2,6-dimethyl-5-heptenyl, 3-(p-isopropyl-phenyl)-2-propyl, (3,7-dimethyl-oct-6-enyloxy)-methyl, (5Z)-octa-1,5-dienyl, 1-nonenyl, 1-undecenyl, 2,6-dimethyl-hepta-1,5-dienyl, 2,6-dimethyl-octa-1,5-dienyl, or $R^2$ and $R^4$ are methyl, and $R^3$=$R^5$ are pentyl, hexyl, heptyl, octyl, nonyl, 2-phenyl-ethyl, 4-methyl-pent-3-ene-1-yl, 4,8-dimethyl-nona-3,7-dien-1-yl, (2,6,6-trimethylcyclohex-1-ene-1-yl)-ethyl, (2,6,6-trimethyl cyclohex-1-ene-2-yl)-ethyl, 2-(4-hydroxyphenyl)-ethyl, (1,3-benzodioxole-5-yl)-ethyl, or $R^2$ and $R^4$ are ethyl, and $R^3$=$R^5$ are 5-methyl-hex-4-en-2-yl, or $R^2$CHR$^3$=$R^4$CHR$^5$ are 2-heptyl-cyclopentyl, 7-methyl-3,4-dihydro-2H-1,5-benzodioxepin-3-yl, 3-methyl-cyclopentadecyl, cyclopentadecyl, 5-cyclohexadecen-1-yl, 4-(1,1-dimethylpropyl)-cyclohexyl, 2-(2-methylethyl)-5-methyl-cyclohexyl, 2-(1-methylethyl)-5-methyl-cyclohexyl, 2-(butan-2-yl)-cyclohexyl, 3-(2-oxo-propyl)-2-pentyl-cyclopentyl, 2-pentyl-3-(methoxycarbonylmethyl)-cyclopentyl.

42. A consumer product comprising a compound of formula I as defined in claim 41.

43. A consumer product according to claim 42 wherein the product is a fine fragrance, home care product, or personal care product.

44. A compound of formula I according to claim 43 wherein $R^1$ is H.

45. A process according to claim 1 wherein $R^1$ is H.

46. A consumer product comprising compound of formula I

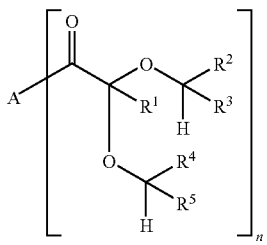
(I)

the compound of formula I which cleaves when exposed to light to form a ketone of formula II,

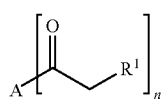
(II)

to form an aldehyde or ketone of the formula III comprising up to 20 carbon atoms, and

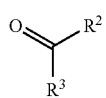
(III)

to form an aldehyde or ketone of the formula IV comprising up to 20 carbon atoms,

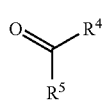
(IV)

wherein A, $R^1$, $R^2$, $R^3$, $R^4$, $R^5$ and n are as defined in claim 1 and with the proviso that A is not phenyl.

47. The consumer product of claim 46 wherein $R^1$ is H.

48. A process for making a ketone of the formula II,

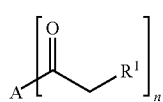
(II)

and an aldehyde or ketone of the formula III comprising up to 20 carbon atoms, and

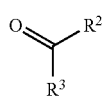
(III)

and an aldehyde or ketone of the formula IV comprising up to 20 carbon atoms,

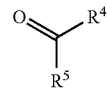
(IV)

which comprise the step of subjecting to a photoreaction a compound of formula I

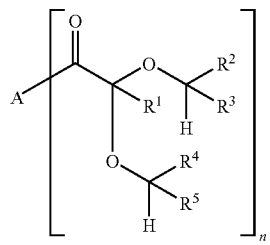
(I)

wherein in the foregoing:

n is 1, $R^1$ is H, methyl, phenyl,

A is phenyl, 6-tert-butyl-1,1-dimethyl-indan-4-yl, 2,4-dimethylphenyl, 3,5,5,6,8,8-hexamethyl-5,6,7,8-tetrahydro-naphthalen-2-yl, 5,6,7,8-tetrahydro-2-naphthalenyl, 1,1,2,3,3-pentamethyl-indan-5-yl, 2-naphthalenyl, 1,1,2,3,3,6-hexamethyl-indan-5-yl, 1,1,2,6-tetra-methyl-3-(1-methylethyl)-indan-5-yl, 3,5,5,8,8-pentamethyl-5,6,7,8-tetrahydro-naphthalen-2-yl, 3-ethyl-5,5,8,8-tetramethyl-5,6,7,8-tetrahydro -naphthalen-2-yl, 4-alkoxy-phenyl, 4-dialkylamino-phenyl, 4-acylamino-phenyl, 4-diacylamino-phenyl, 3,4-(methylenedioxy)-phenyl, 3,4-dialkoxy-phenyl, 4-(2-methoxyethoxy)-phenyl, 3,4-di-(2-methoxyethoxy)-phenyl, 4-[2-(2-methoxyethoxy)-ethoxy]-phenyl, 3,4-di-[2-(2-methoxyethoxy)-ethoxy]-phenyl, 2,3-dihydro-benzo[1,4]dioxin-6-yl, $R^2$ and $R^4$ are hydrogen, and $R^3$=$R^5$ are 6,10-dimethylundec-9-ene-2-yl, 2,4-dimethyl-cyclohex-3-ene-1-yl, 1,3,5-trimethyl-cyclohex-1-ene-4-yl, 4-(4-hydroxy-4-methyl-pentyl)-cyclohex-3-ene-1-yl, pent-1-enyl, hexyl, 6-methyl-hept-5-ene-2-yl, nonyl, 2-decyl, 9-decenyl, decyl, undecyl, 2-undecyl, heptyl, octyl, 8-decenyl, 1-phenyl-ethyl, (4-methyl-phenyl)-methyl, 2,6-dimethyl-heptyl, 2,6,10-trimethyl-undeca-5,9-dienyl, 2,6-dimethyl-6-hydroxy-heptyl, 2-(3-isopropyl-phenyl)-propyl, 4-(4-methyl-pent-3-enyl)-cyclohex-3-ene-1-yl, 4-(2,6,6-trimethylcyclohex-2-en-1-yl)-2-butyl, 3-(4-tert-butylphenyl)-2-propyl, 2-(4-tert-butylphenyl)-ethyl, 3-(benzo [1,3]dioxol-5-yl)-2-propyl, 2,6-dimethyl-5-heptenyl, 3-(p-isopropyl-phenyl)-2-propyl, (3,7-dimethyl-oct-6-enyloxy)-methyl, (5Z)-octa-1,5-dienyl, 1-nonenyl, 1-undecenyl, 2,6-dimethyl-hepta-1,5-dienyl, 2,6-dimethyl-octa-1,5-dienyl, or $R^2$ and $R^4$ are methyl, and $R^3$=$R^5$ pentyl, hexyl, heptyl, octyl, nonyl, 2-phenyl-ethyl, 4-methyl-pent-3-ene-1-yl, 4,8-dimethyl-nona-3,7-dien-1-yl, (2,6,6-trimethylcyclohex-1-ene-1-yl)-ethyl, (2,6,6-trimethyl cyclohex-1-ene-2-yl)-ethyl, 2-(4-hydroxyphenyl)-ethyl, (1,3-benzodioxole-5-yl)-ethyl, or $R^2$ and $R^4$ are ethyl, and $R^3$=$R^5$ are 5-methyl-hex-4-en-2-yl, or R²CHR³=R⁴CHR⁵ are 2-heptyl-cyclopentyl, 7-methyl-3,4-dihydro-2H-1,5-benzodioxepin-3-yl, 3-methyl-cyclopentadecyl, cyclopentadecyl, 5-cyclohexadecen-1-yl, 4-(1,1-dimethylpropyl)-cyclohexyl, 2-(2-methylethyl)-5-methyl-cyclohexyl, 2-(1-methylethyl)-5-methyl-cyclohexyl, 2-(butan-2-yl)-cyclohexyl, 3-(2-oxo-propyl)-2-pentyl-cyclopentyl, 2-pentyl-3-(methoxycarbonylmethyl)-cyclopentyl.

49. A compound selected from the group:

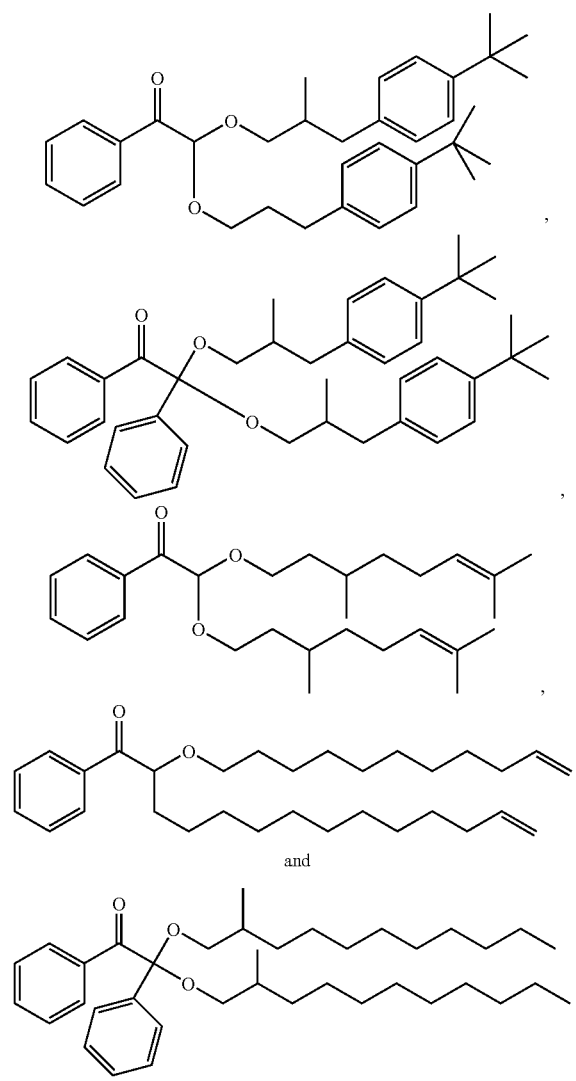

50. A consumer product comprising a compound selected from the group consisting of:

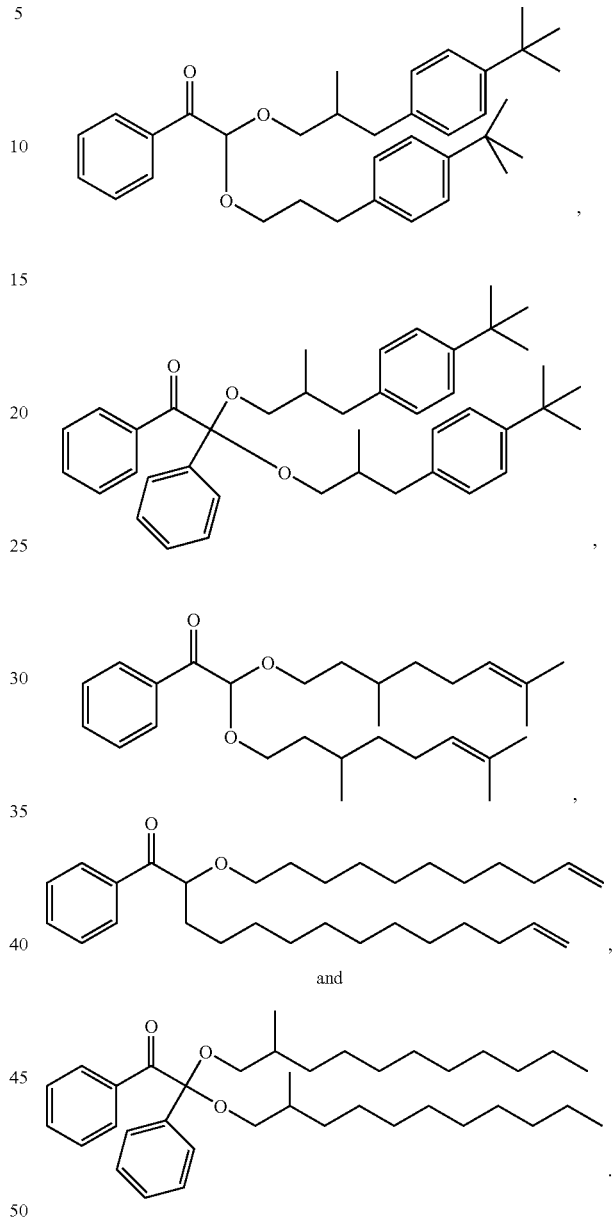

* * * * *